United States Patent
Tomich et al.

(10) Patent No.: US 6,713,260 B2
(45) Date of Patent: Mar. 30, 2004

(54) METHODS OF IDENTIFYING COMPOUNDS THAT BIND TO TARGET SPECIES UNDER ISOTHERMAL DENATURING CONDITIONS

(75) Inventors: Paul K. Tomich, Kalamazoo, MI (US); Dennis E. Epps, Portage, MI (US); Ferenc J. Kezdy, Kalamazoo, MI (US); Charles K. Marschke, Kalamazoo, MI (US); Ronald W. Sarver, Paw Paw, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 168 days.

(21) Appl. No.: 10/008,090

(22) Filed: Nov. 13, 2001

(65) Prior Publication Data

US 2002/0068298 A1 Jun. 6, 2002

Related U.S. Application Data

(63) Continuation of application No. 09/458,171, filed on Dec. 9, 1999, now Pat. No. 6,376,180.

(51) Int. Cl.$^7$ ............................................. G01N 33/52
(52) U.S. Cl. ................ 435/6; 422/55; 422/58; 422/68.1; 422/82.05; 422/82.08; 422/82.11; 435/4; 435/7.1; 435/287.1; 435/287.2; 435/288.3; 435/288.4; 435/288.7; 435/808; 436/172; 436/173; 436/518; 436/524; 436/527; 436/805; 436/50; 356/246; 356/317; 356/318
(58) Field of Search ............... 435/4, 6, 7.1, 287.1, 435/287.2, 288.3, 288.4, 288.7, 808; 436/518, 524, 527, 172, 173, 805, 50; 422/55, 58, 68.1, 82.05, 82.08, 82.11; 356/317, 318, 246

(56) References Cited

U.S. PATENT DOCUMENTS

| | | | |
|---|---|---|---|
| 3,939,350 A | * | 2/1976 | Kronick et al. .............. 436/805 |
| 5,585,277 A | | 12/1996 | Bowie et al. |
| 5,679,582 A | | 10/1997 | Bowie et al. |
| 6,020,141 A | | 2/2000 | Pantoliano et al. |
| 6,036,920 A | | 3/2000 | Pantoliano et al. |
| 6,242,190 B1 | | 6/2001 | Freire et al. |

FOREIGN PATENT DOCUMENTS

| | | |
|---|---|---|
| EP | 0770876 A | 5/1997 |
| WO | WO 97/20952 A1 | 6/1997 |
| WO | WO 97/42500 | 11/1997 |
| WO | WO 98/16814 | 4/1998 |
| WO | WO 99/29894 | 6/1999 |

OTHER PUBLICATIONS

Petersen, "Diffusion and aggregation in biological membranes," *Can J Biochem Cell Biol.* Nov. 1984; 62(11):1158–66.

Trier et al., "Fusion of the binding domain of Raf–1 kinase with green fluorescent protein for activated Ras detection by fluorescence correlation spectroscopy," *Pharmazie.* Apr. 1999; 54(4):263–8.

Babu et al., "Ionic–strength–dependent transition of hen egg–white lysozyme at low pH to a compact state and its aggregation on thermal denaturation," *Eur. J. Biochem.,* 245:781–789 (1997).

Berland et al., "Two–Photon Fluorescence Correlation Spectroscopy: Method and Application to the Intracellular Environment," *Biophys. J.,* 68(2):694–701 (1995).

Berland et al., "Scanning Two–Photon Fluctuation Correlation Spectroscopy: Particle Counting Measurements for Detection of Molecular Aggregation," *Biophys. J.,* 71:410–420 (1996.

S. I. Blaber et al., "Reversible Thermal Denaturation of Human FGF–1 Induced by Low Concentrations of Guanidine Hydrochloride," *Biophysical Journal,* 77, 470–477 (1999).

Brandts, "The Thermodynamics of Protein Denaturation. I. The Denaturation of Chymotrypsinogen," *J. Am. Chem. Soc.,* 86:4291–4301 (1964).

Brandts, "The Thermodynamics of Protein Denaturation. II. A Model of Reversible Denaturation and Interpretations Regarding the Stability of Chymotrypsinogen," *J. Am. Chem. Soc.,* 86:4302–4314 (1964).

Brandts et al., "The Thermodynamics of Protein Denaturation. III. The Denaturation of Ribonuclease in Water and in Aqueous Urea and Aqueous Ethanol Mixtures," *J. Am. Chem. Soc.,* 89(19):4826–4838 (1967).

Carl Zeiss, Homepage, www.zeiss.de/mi/fcs_e/lit_e.html 1 page (2000).

Chan et al., "Effects of Additives on Heat Denaturation of rhDNase in Solutions," *Pharm. Res.,* 13(5):756–761 (1996).

Chen et al., "The Photon Counting Histogram in Fluorescence Fluctuation Spectroscopy," *Biophys. J.,* 77(1):553–567 (1999).

(List continued on next page.)

*Primary Examiner*—Christopher L. Chin
(74) *Attorney, Agent, or Firm*—Mueting, Raasch & Gebhardt, P.A.

(57) ABSTRACT

The present invention provides a method for identifying a test compound that binds to a target species. The method includes: incubating at least one test mixture under isothermal denaturing conditions, each test mixture comprising at least one test compound, and at least one target species, wherein the isothermal denaturing conditions are effective to cause at least a portion of the target species to denature to a measurable extent; detecting a denaturation signal of each target species in the presence of the at least one test compound by a change in the diffusion properties of the target molecule using fluorescence correlation spectroscopy; and comparing the denaturation signal of each target species in the presence of at least one test compound with a denaturation signal of the same target species in the absence of the at least one test compound under the same isothermal denaturing conditions.

16 Claims, 11 Drawing Sheets

OTHER PUBLICATIONS

Figure 1:
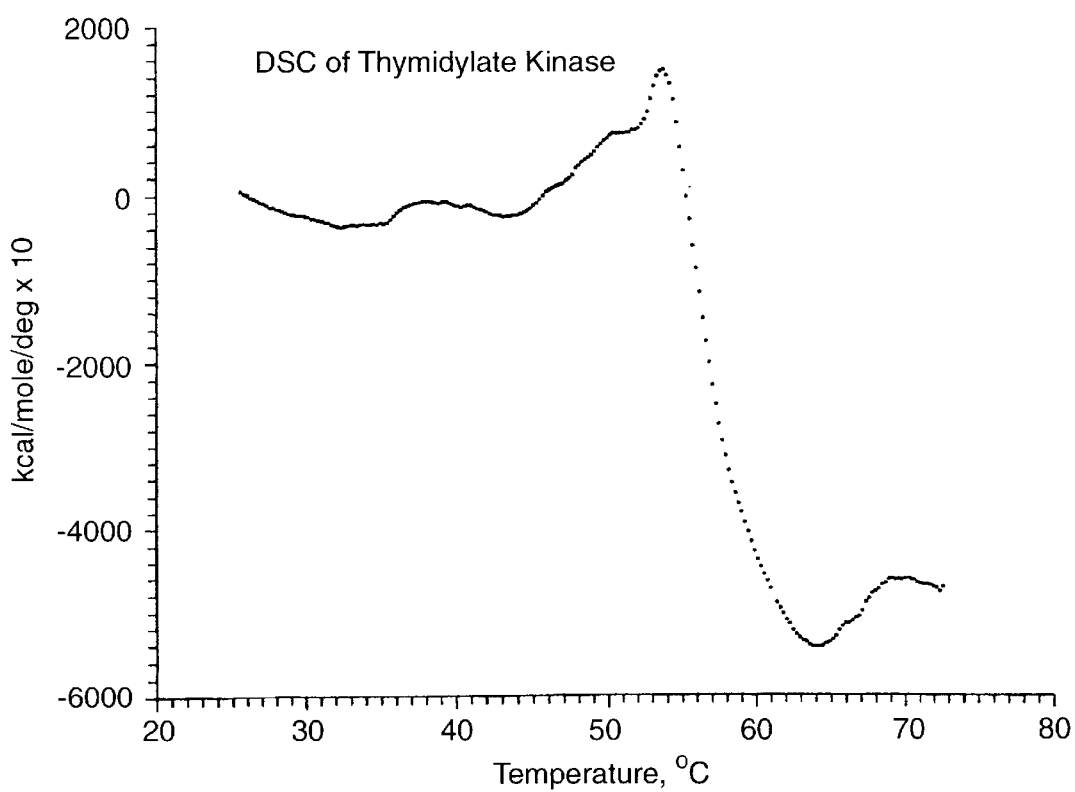

Cho et al., "The Binding Site of a Specific Aminoglycoside Binding RNA Molecule," *Biochemistry,* 37(14):4985–4992 (1998).

Douthwaite et al., "Erythromycin Binding is Reduced in Ribosomes with Conformational Alterations in the 23 S rRNA Peptidyl Transferase Loop," *J. Mol. Biol.,* 232:725–731 (1993).

Egebjerg et al., "Binding sites of the antibiotics pactamycin and celesticetin on ribosomal RNAs," *Biochimie,* 73:1145–1149 (1991).

Ehlert et al., "Specifications of FemA and FemB for Different Glycine Residues: FemB Cannot Substitute for FemA in Staphylococcal Peptidoglycan Pentaglycine Side Chain Formation," *J. Bacteriol.,* 179(23):7573–7576 (1997).

Elson et al., "Concentration Correlation Spectroscopy: A New Biophysical Probe Based on Occupation Number Fluctuations," *Annu. Rev. Biophys. Bioeng.,* 4:311–334 (1975).

Epps et al., "The Constituent Tryptophans and bis ANS as Fluorescent Probes of the Active Site and of a Secondary Binding Site of Stromelysin–1 (MMP–3)," *J. Prot. Chem.,* 17(7):699–712 (1998).

Ferrer et al., "Partially folded, molten globule and molten coil states of bovine pancreatic trypsin inhibitor," *Structural Biology,* 2(3):211–217 (1995).

Finzel et al., "Structural characterizations of nonpeptide thiadiazole inhibitors of matrix metalloproteinases reveal the basis for stromelysin selectivity," *Prot. Sci.,* 7:2118–2126 (1998).

Foster et al., "Pharmacological Rescue of Mutant p53 Conformation and Function," *Science,* 286(5449):2507–2510 (1999).

Gloss et al., "Urea and Thermal Equilibrium Denaturation on the Dimerization of *Escherichia coli* Trp Repressor," *Biochemistry,* 36(19):5612–5623 (1997).

Graziano et al., DSC study of the thermal stability of S–protein and S–peptide/S–protein complexes, *Biochem.,* 35:13386–13392 (1996).

Handbook of Fluorescent Probes and Research Chemicals, "3.2 Hydrazines and Aromatic Amines for Modifying Aldehydes and Ketones," www.probes.com/handbook/sections/0302.html, 5 pages (page updated Feb. 4, 2000).

He et al., "Comparison of Inactivation and Unfolding of Yeast Alcohol Dehydrogenase During Thermal Denaturation," *Int. J. Biochem. Cell Biol.,* 29(7):1021–1028 (1997).

Ibarra–Molero et al., "Thermal versus Guanidine–Induced Unfolding of Ubiquitin. An analysis in Terms of the Contributions from Charge—Charge Interactions to Protein Stability," *Biochemistry,* 38(25):8138–8149 (1999).

Imai, "Purification and Characterization of a Pyridine Nucleotide Glycohydrolase from Rabbit Spleen," *J. Biochem.,* 106(5):928–937 (1989).

Jones et al., "New Fluorescent Assay for Detection and Quantitation of Nanogram Levels of Proteins in Solution," *FASEB J.,* p. A1512, abstract 2954, 2 pages (1996).

Kam et al., "Simple schemes for measuring autocorrelation functions," *Rev. Sci. Instrum.,* 46(3):269–277 (1975).

Kettling et al., "Real–time enzyme kinetics monitored by dual–color fluorescence cross–correlation spectroscopy," *Proc. Natl. Acad. Sci. USA,* 95:1416–1420 (1998).

Kotik et al., "Evidence for Temperature–Dependent Conformational Changes in the L–Lactate Dehydrogenase from *Bacillus stearothermophilus,*" *Biochemistry,* 31(34):7787–7795 (1992).

Kurganov et al., "Analysis of differential scanning calorimetry data for proteins: Criteria of validity of one–step mechanism of irreversible protein denaturation," *Biophys. Chem.,* 69:125–135 (1997).

Lavie et al., "Structure of thymidylate kinase reveals the cause behind limiting step in AZT activation," *Nature Structural Biology,* 4(8):601–604 (1997).

Leviev et al., "A conserved secondary structural motif in 23S rRNA defines the site of interaction of amicetin, a universal inhibitor of peptide bond formation," *EMBO J.,* 13(7):1682–1686 (1994).

Maiti et al., "A study of protein folding with two–photon fluorescence correlation spectroscopy," *Biophysical Journal,* 70(2):part 2, A262 (Feb. 17–21, 1996).

Mei et al., "Inhibitors of Protein–RNA Complexation That Target the RNA: Specific Recognition of Human Immunodeficiency Virus Type 1 TAR RNA by Small Organic Molecules," *Biochemistry,* 37(40):14204–14212 (1998).

Merkler et al., "Aggregation and thermo–inactivation of glutamine synthetase from an extreme thermophile, *Bacillus caldolyticus,*" *Biochim. Biophys. Acta,* 952:101–114 (1988).

Mildner et al., "The HIV–1 Protease as Enzyme and Substrate: Mutagenesis of Autolysis Sites and Generation of a Stable Mutant with Retained Kinetic Properties," *Biochemistry,* 33(32):9405–9413 (1994).

Moore et al., "Single Molecule Detection Technologies in Miniaturized High Throughput Screening: Fluorescence Correlation Spectroscopy," *J. Biomol. Screening,* 4(6):335–353 (1999).

Moses et al., "Basic Pancreatic Trypsin Inhibitor has Unusual Thermodynamic Stability Parameters," *J. Mol. Biol.,* 170:765–776 (1983).

Narhi et al., "Reversibility of heat–induced denaturation of the recombinant human megakaryocyte growth and development factor," *Pharm. Res.,* 16(6):799–807 (1999).

Payne et al., "Ligand stabilization of cholinesterases," *Biochim. Biophys. Acta,* 999:46–51 (1989).

Petersen et al., "[19] Measurements of Diffusion and Chemical Kinetics by Fluorescence Photobleaching Recovery and Fluorescence Correlation Spectroscopy," *Methods in Enzymol.,* 130: 454–484 (1986).

Poklar et al., "pH and Temperature–Induced Molten Globule–Like Denatured States of Equinatoxin II: A Study by UV–Melting, DSC, Far– and Near–UV CD Spectroscopy, and ANS Fluorescence," *Biochemistry,* 36(47):14345–14352 (1997).

Prostasevich et al., "Comparative Study of Monoclonal Immunoglobulin M and Rheumatoid Immunoglobulin M by Differential Scanning Microcalorimetry," *Biochemistry (Moscow),* 62(8):914–918, Translated from *Biokhimiya,* 62(8):1066–1071 (1997).

Rauer et al., "Fluorescence correlation spectrometry of the interaction kinetics of tetramethylrhodamin α–bungarotoxin with *Torpedo californica* acetlycholine receptor," *Biophys. Chem.,* 58:3–12 (1996).

Rigler, "Fluorescence correlations, single molecule detection and large number screening, Applications in biotechnology," *Journal of Biotechnology,* 41, 177–186 (1995).

Rosendahl et al., "The antibodies micrococcin and thiostrepton interact directly with 23S rRNA nucleotides 1067A and 1095A," *Nuc. Acids Res.,* 22(3):357–363 (1994).

Ruvinov et al., "Ligand–mediated Changes in the Tryptophan Synthase Indole Tunnel Probed by Nile Red Fluorescence with Wild Type, Mutant, and Chemically Modified Enzymes," *J. Biol. Chem.*, 270(11):6357–6369 (1995).

Sackett et al., "Nile Red as a Polarity–Sensitive Fluorescent Probe of Hydrophobic Protein Surfaces," *Anal. Biochem.*, 167:228–234 (1987).

Sackett et al., "Hydrophobic Surfaces of Tubulin Probed by Time–resolved and Steady–state Fluorescence of Nile Red," *J. Biol. Chem.*, 265(25):14899–14906 (1990).

Sarver et al., "Thermodynamic and circular dichroism and studies differentiate inhibitor interactions with the stromelysin $S_1$–$S_3$ and $S'_1$–$S'_3$ subsites," *Biochim. Biophys. Acta*, 1434:304–316 (1999).

Shosheva et al., "Urea unfolding and stability of gamma–II crystalline," *J. Photochem. Photobiol. B: Biol.*, 21, 183–189 (1993).

Sontum et al., "Photon correlation spectroscopy applied to characterisation of denaturation and thermal stability of human albumin," *J. Pharm. Biomed. Anal.*, 16:295–302 (1997).

Spickler et al., "Streptomycin Binds to the Decoding Center of 16 S Ribosomal RNA," *J. Mol. Biol.*, 273:586–599 (1997).

Steinberg et al., "SYPRO Orange and SYPRO Red Protein Gel Stains: One–Step Fluorescent Staining of Denaturing Gels for Detection of Nanogram Levels of Protein," *Anal. Biochem.*, 239:223–237 (1996).

Steinberg et al., "Application of SYPRO Orange and SYPRO Red Protein Gel Stains," *Anal. Biochem.*, 239:238–245 (1996).

Sterrer et al., "Fluorescence Correlation Spectroscopy (FCS): A Highly Sensitive Method to Analyze Drug/Target Interactions," *J. of Receptor & Signal Transduction Research*, 17:(1–3), 511–520 (1997).

Szeltner et al., "Conformational Stability and Catalytic Activity of HIV–1 Protease Are Both Enhanced at High Salt Concentration," *J. Biol. Chem.*, 271(10):5458–5463 (1996).

Thompson et al., "Immunoglobulin surface–binding kinetics studied by total internal reflection with fluorescence correlation spectroscopy," *Biophys. J.*, 43, 103–114 (1983).

Tschierske et al., "Lif, the lysostaphin immunity factor, complements FemB in staphylococcal peptidoglycan interpeptide bridge formation," *FEMS Microbiol. Lett.*, 153:261–264 (1997).

Tuerk et al., "Systematic Evolution of Ligands by Exponential Enrichment: RNA Ligands to Bacteriophage T4 DNA Polymerase," *Science*, 249:505–510 (1990).

Uversky et al., "Use of fluorescence decay times of 8–ANS–protein complexes to study the conformational transitions in proteins which unfold through the molten globule state," *Biophys. Chem.*, 60:79–88 (1996).

Werstuck et al., "Controlling Gene Expression in Living Cells through Small Molecule–RNA Interactions," *Science*, 282:296–298 (1998).

Wong et al., "Specificity of aminoglycoside antibiotics for the A–site of the decoding region of ribosomal RNA," *Chemistry & Biology*, 5:397–406 (1998).

Yamaoka et al., "A pharmacokinetic analysis program (multi) for microcomputer," *J. Pharm. Dyn.*, 4(11):879–885 (1981).

* cited by examiner

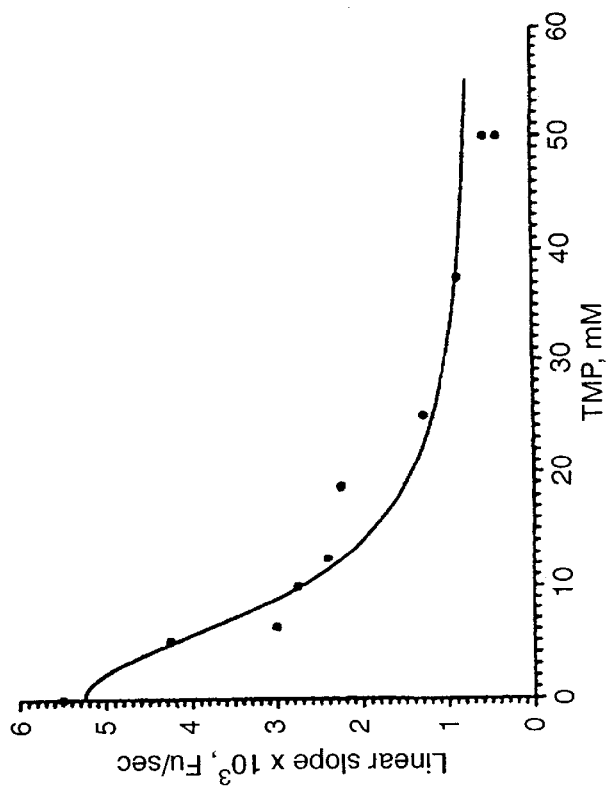
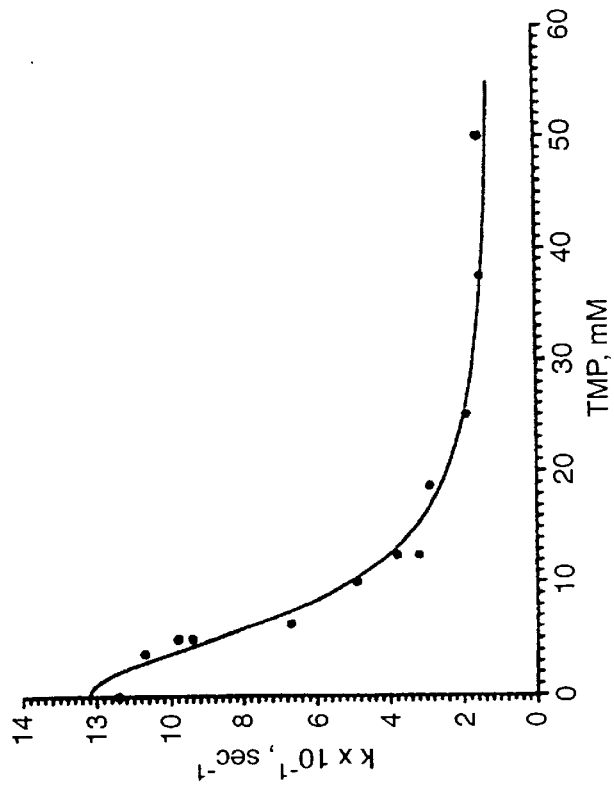
Fig. 5A
Fig. 5B

METHODS OF IDENTIFYING COMPOUNDS THAT BIND TO TARGET SPECIES UNDER ISOTHERMAL DENATURING CONDITIONS

This is a continuation of application Ser. No. 09/458,171, filed Dec. 9, 1999, now U.S. Pat. No. 6,376,180, issued on Apr. 23, 2002, which is incorporated herein by reference.

BACKGROUND OF THE INVENTION

One of the major challenges facing the drug discovery process is the identification of small organic ligands that will bind to target species, particularly protein targents. A multitude of new protein targets are being discovered by genomics and bioinformatics efforts. Many of these proteins have no known function or known specific ligands. Thus, the identification of ligands for these targets presents challenges in the screening of large chemical libraries by high throughput screening (HTS), including ultra-high throughput screening (UHTS), methods, particularly from the standpoint of assay development. Hence, there is a need for a straightforward, generally applicable methodology, particularly an HTS assay methodology, that can be used to identify ligands that bind proteins, especially those with unknown functionality.

It is known that the binding of substrates or specific ligands does, in general, alter the intrinsic stability and hence the denaturation profile of a protein. Thus, methods that measure protein denaturation can be used to detect and quantitate ligand-protein interactions.

The denaturation of proteins is accompanied by the progressive loss of their tertiary/quaternary structure and ultimately biological activity. Denaturation can be accomplished by a number of physical and chemical methods that involve changes in temperature, pH, and/or, ionic strength, use of chaotropic agents, etc. It can be followed by methods sufficiently sensitive to monitor conformational changes in a protein. Because it is a simple and widely applicable experimental method, thermal denaturation has been used for a variety of purposes, including purifying proteins by selective denaturation of impurities and to study protein structure, folding, and stability. Thermal denaturation curves ((TDC), where the fraction of denatured protein is measured as a function of gradually increasing temperatures) obtained by differential scanning calorimetry (DSC) have been shown to be particularly useful for determining protein stability and making inferences about the tertiary structure. The usefulness of TDC is further enhanced because binding of compounds that are substrates or specific ligands for a given protein changes the intrinsic stability of that protein and, hence, causes a shift in the TDC and the $T_m$ (midpoint temperature) values.

Interpretation of the results of thermal scanning methods depends on the assumption that the denaturation process is a one-step, reversible, and continuous process that is very rapid on the time scale of the temperature scanning rate. However, the denaturation of most proteins under the usual experimental conditions is irreversible. Typically, it is only with small proteins and very mild denaturing agents that denaturation is readily reversible. Thus, DSC may be unable to provide reproducible and readily interpretable binding measurements.

In general, the DSC curves reflect the stability of many different structural domains, some sensitive to the binding of ligands and some not sensitive at all. Furthermore, denaturation may be initiated at many locations within the protein structure. Each of these processes has its own activation energy, which makes it the dominant process only within a narrow temperature range. As a consequence, depending on the scanning rate, the stability of a given domain may or may not be evident in the DSC curve. Furthermore, differential scanning calorimetry may see two or more protein denaturation steps where one would expect only a single transition. Yet another major factor contributing to the greater inextricability of the scanning thermal denaturation methods is that the binding equilibria of both the ligands of interest and of the fluorescent dyes reporting on the structural integrity of the protein are strongly temperature dependent. Thus, both the sensitivity of the method and the stabilizing effect of the ligand under study drift drastically during the experiment.

Therefore, a need exists for a method identifying compounds that bind to target species. Preferably, such a method is amenable to UHTS or HTS, reproducible, and independent of the heating rate.

SUMMARY OF THE INVENTION

The present invention provides methods for identifying compounds that bind to target species (e.g., polypeptides including proteins, and polynucleotides including DNA and RNA). These methods involve the use of isothermal denaturation, preferably in combination with fluoresence detection methods. Significantly, the methods of the present invention involve automated methods suitable for HTS and UHTS. Ideally, the methods of the present invention are envisioned to be scalable to evaluate 10,000–60,000 compounds or more in a 24 hour period.

Isothermal denaturation of proteins offers an attractive method for the identification of binding ligands. Significantly, in preferred methods, the present invention couples fluorescence techniques with denaturation by isothermal methods to determine alteration of target (e.g., protein) stability by a bound ligand. In particularly preferred embodiments, the denaturation and stabilization or destabilization of target species (e.g., protein targets) by ligands against isothermal denaturation is quantified by changes in fluorescence intensity.

In one preferred embodiment, the present invention provides a high throughput screening method for identifying a test compound that binds to a target species. The method includes: incubating a plurality of test mixtures under isothermal denaturing conditions, each test mixture including at least one test compound (preferably, at least two test compounds, and more preferably, 2 to 10 test compounds) and at least one target species (preferably, only one target species is in any one test mixture), wherein the isothermal denaturing conditions are effective to cause at least a portion of the target species to denature (e.g., unfold) to a measurable extent. The method further involves detecting a denaturation signal of each target species in the presence of the at least one test compound; and comparing the denaturation signal of each target species in the presence of the at least one test compound with a denaturation signal of the same target species in the absence of the at least one test compound under the same isothermal denaturing conditions. Typically and preferably, the methods of the present invention can evaluate at least about 100 test mixtures per day. Preferably, such an evaluation occurs substantially simultaneously.

In the methods described herein, the target species can be a polypeptide (e.g., protein) or a polynucleotide (e.g., DNA or RNA). Preferably, the target species is a protein. The compound can bind to the target species either specifically (e.g., at a specific site or in a specific manner) or unspecifically. The binding can involve a variety of mechanisms, including covalent bonding, ionic bonding, hydrogen bonding, hydrophobic bonding (involving van der Waals forces), for example, or combinations thereof.

DEFINITIONS

In the present invention the following definitions apply:

Isothermal denaturing conditions refers to conditions effective to denature a target molecule at a fixed temperature. It can also involve defined conditions with respect to pH, ionic strength, cation concentration, etc., which are generally held constant for evaluation of various compounds for a given target.

Denaturation signal refers to the signal produced by the target species upon being denatured.

$T_m$ refers to the midpoint of the melting transition of the target as determined by differential scanning calorimetry.

Reporter molecule refers to a separately added molecule such as a fluorescent dye or a covalently bonded reporter group attached to the target.

BRIEF DESCRIPTION OF THE FIGS.

FIG. 1. DSC scan of Thymidylate Kinase (TK). The thermal melting profile of thymidylate kinase was determined as described in the Methods.

Figure 2:
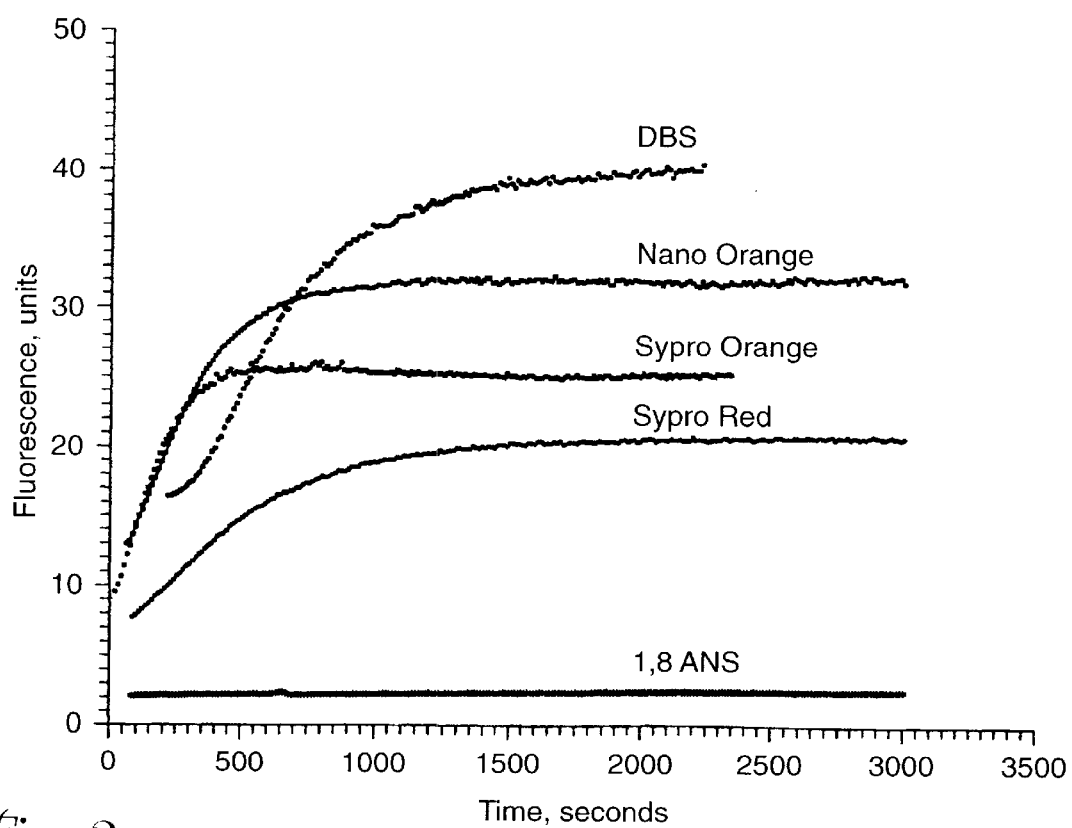

FIG. 2. Isothermal denaturation of TK as monitored by various fluorescent dyes. The isothermal denaturation experiments were performed as described in the Methods at a temperature of 53° C. using a protein concentration of 0.5 $\mu$M. The concentration of DBS was 1 $\mu$M, 1,8-ANS was 2 $\mu$M, and the protein dyes were as follows: Nano Orange was at a 1:650-fold dilution, and both SYPRO Orange and SYPRO Red were at 1:10,0000-fold dilutions.

Figure 3:
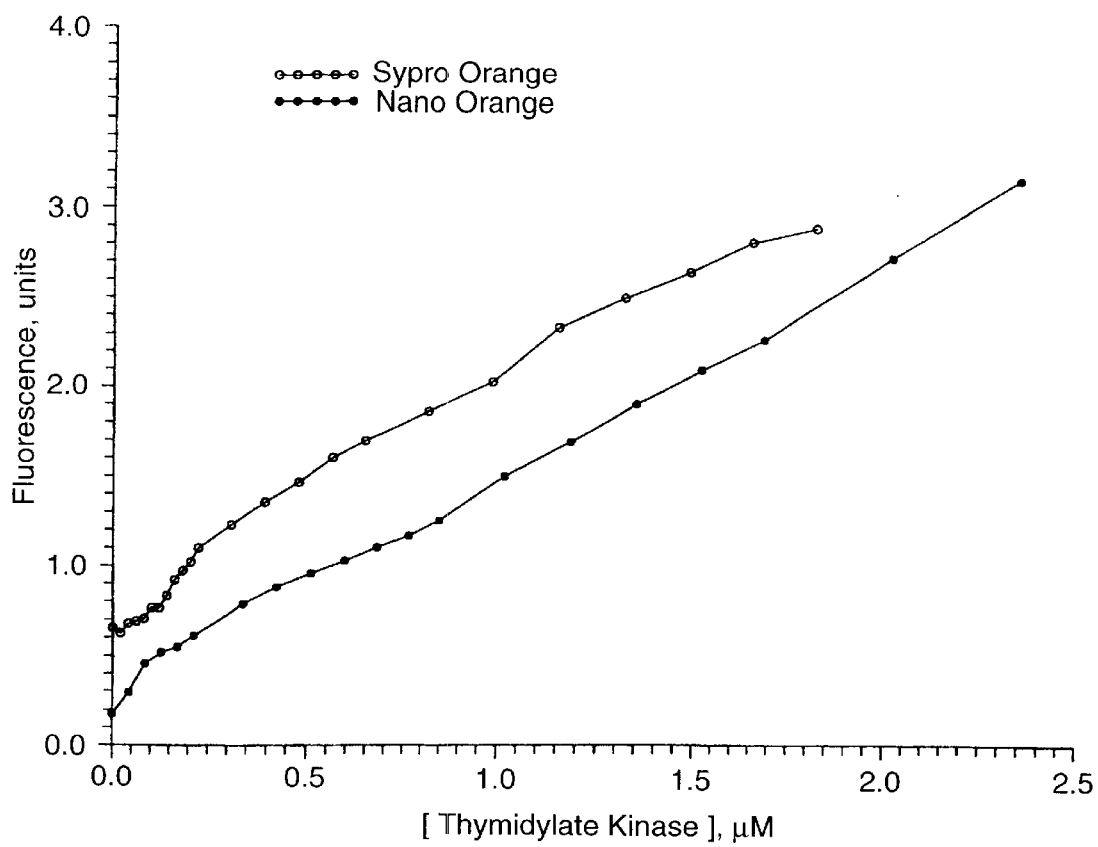

FIG. 3. Titration of SYPRO Orange and Nano Orange with TK. A fixed amount of dye, 250 nM for DBS and a 1:2600 dilution of Nano Orange was titrated at T=23° C. with increasing amounts of thymidylate kinase and the fluorescence increases recorded. The emission/excitation wavelengths used are given in Table 1.

Figure 4:
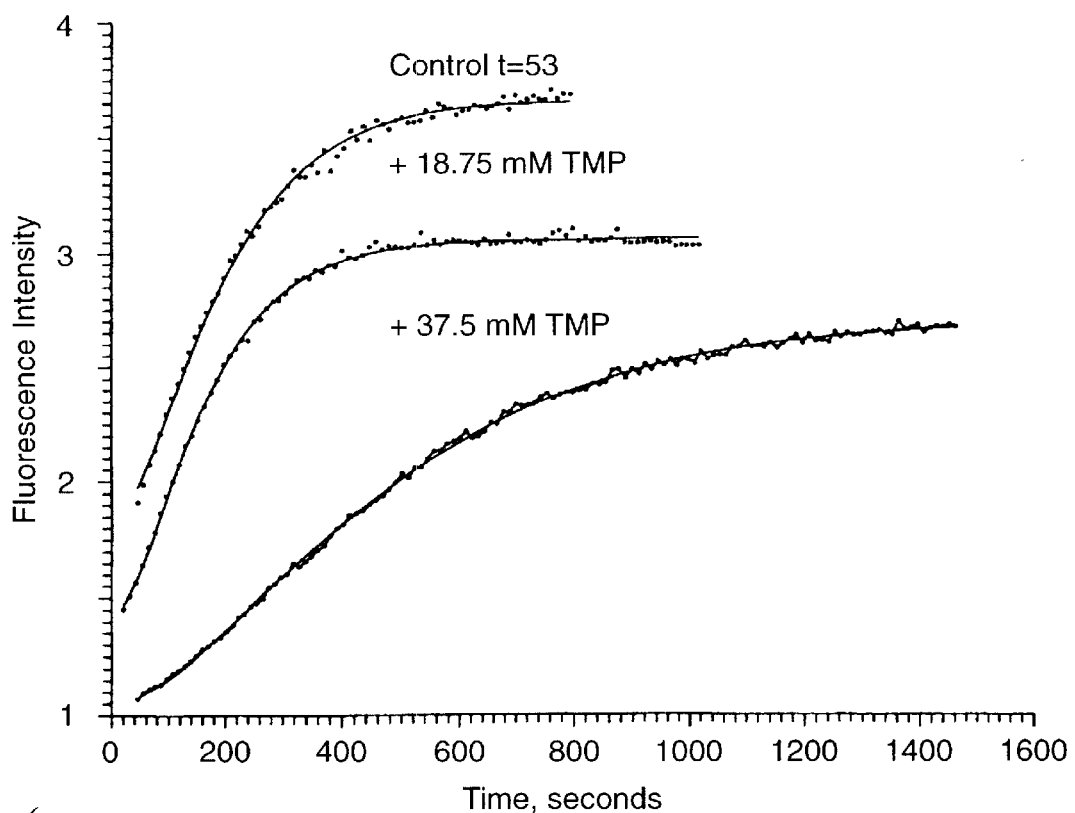

FIG. 4. Time-dependency of the isothermal denaturation of TK in the presence of thymidine monophosphate (TMP) monitored by SYPRO Orange. The experimental denaturation conditions for monitoring the isothermal denaturation of TK by SYPRO Orange fluorescence are described in the Examples. The reaction mixture in 2 mL of buffer contained protein, 0.5 mM, SYPRO Orange, at a 20,000-fold dilution, and TMP at the indicated concentrations. TMP was present in the reaction mixture at the time of the addition of protein.

FIGS. 5A–5B. Dose-dependency of the stabilization of TK against isothermal denaturation by TMP. The dose-dependency of the TMP/TK interaction was calculated using both the linear slopes of the kinetic curves and the first-order rate constants as described in the Results. A second-order Langmuir model was used to calculate the dissociation constants from the slope and rate constant values. The solid line represents the theoretical fit to the experimental data points. The TMP dose-dependent stabilization of thymidylate kinase as measured by the first-order rate constants is shown in FIG. 5A and by initial rates in FIG. 5B.

Figure 6:
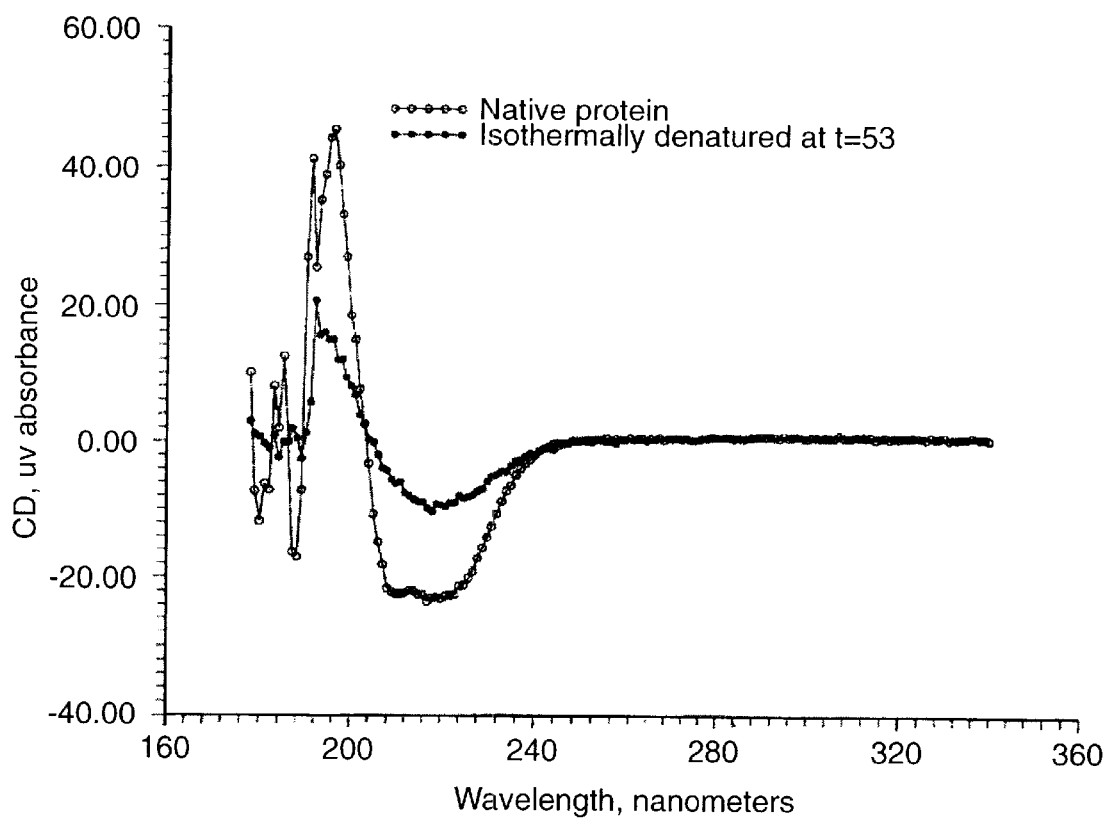

FIG. 6. Effect of isothermal denaturation of the CD (Circular Dichroism) structure of TK. The CD spectra of native and isothermally denatured TK were taken as described in the Methods; open circles= native protein; solid circles=TK isothermally denatured at T=53° C.

Figure 7:
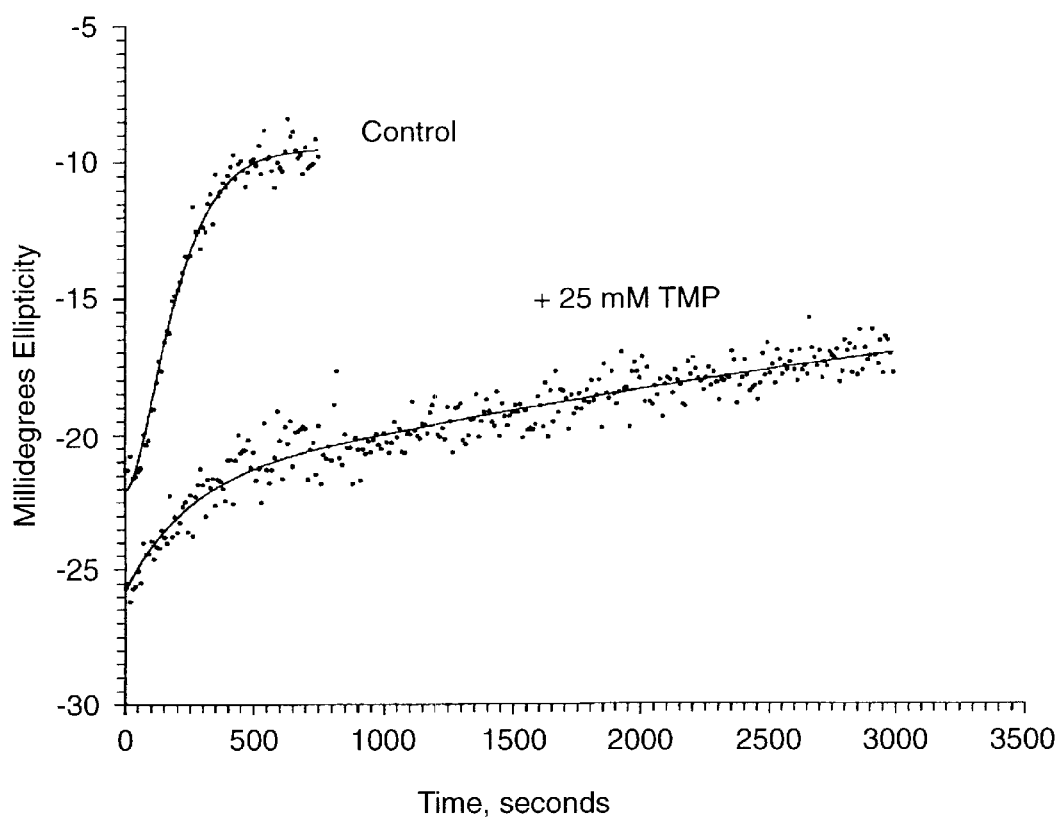

FIG. 7. Time-dependency of the isothermal denaturation of TK monitored by CD. The time-dependency of TK isothermal denaturation at 53° C. with or without the addition of 25 mM TMP was followed by CD as described in the Examples. The data were analyzed using a first-order rate model and the solid lines represent the theoretical fits to the experimental data points.

Figure 8:
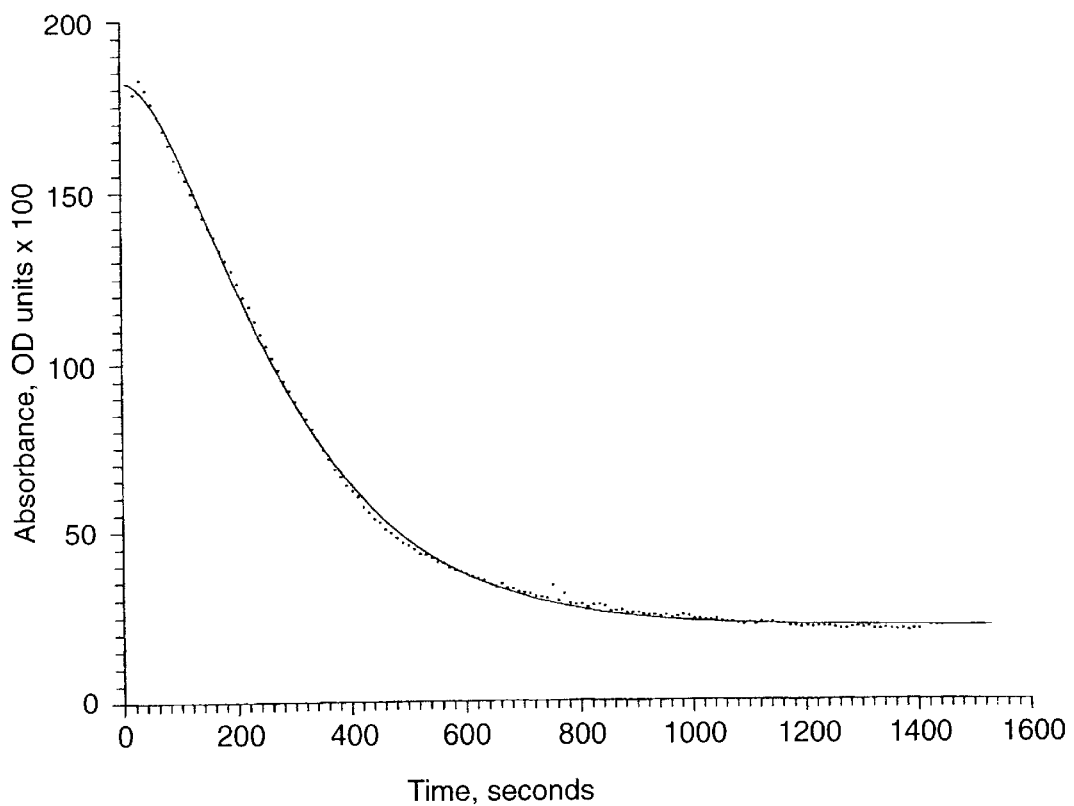

FIG. 8. Time-dependency of the isothermal denaturation of TK monitored by UV Hyperchromicity. The time-dependency of TK isothermal denaturation was monitored by the absorbance increase at 280 nm as described in the Examples. The data were analyzed using Equation 4 (below) and the solid line represents the theoretical fit to the experimental data points.

Figure 9:
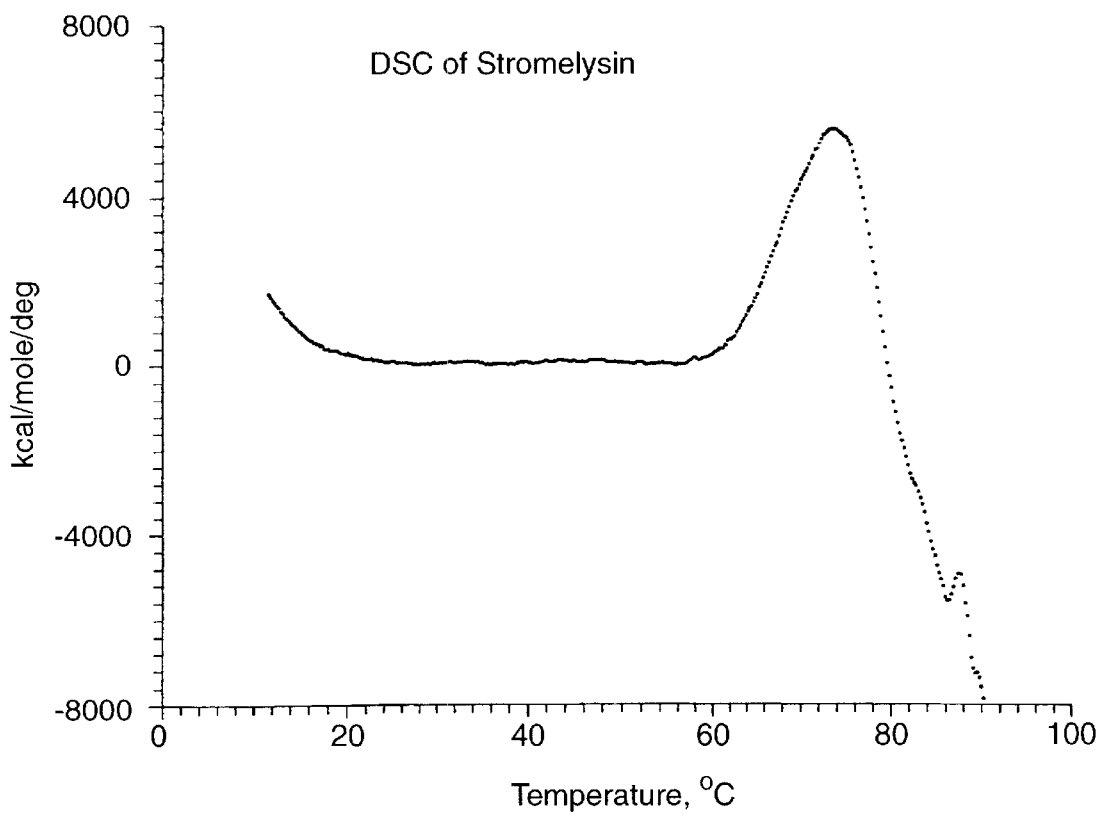

FIG. 9. DSC Scan of Stromelysin. The thermal melting profile of stromelysin was determined as described in the Methods.

Figures 10A, 10B:
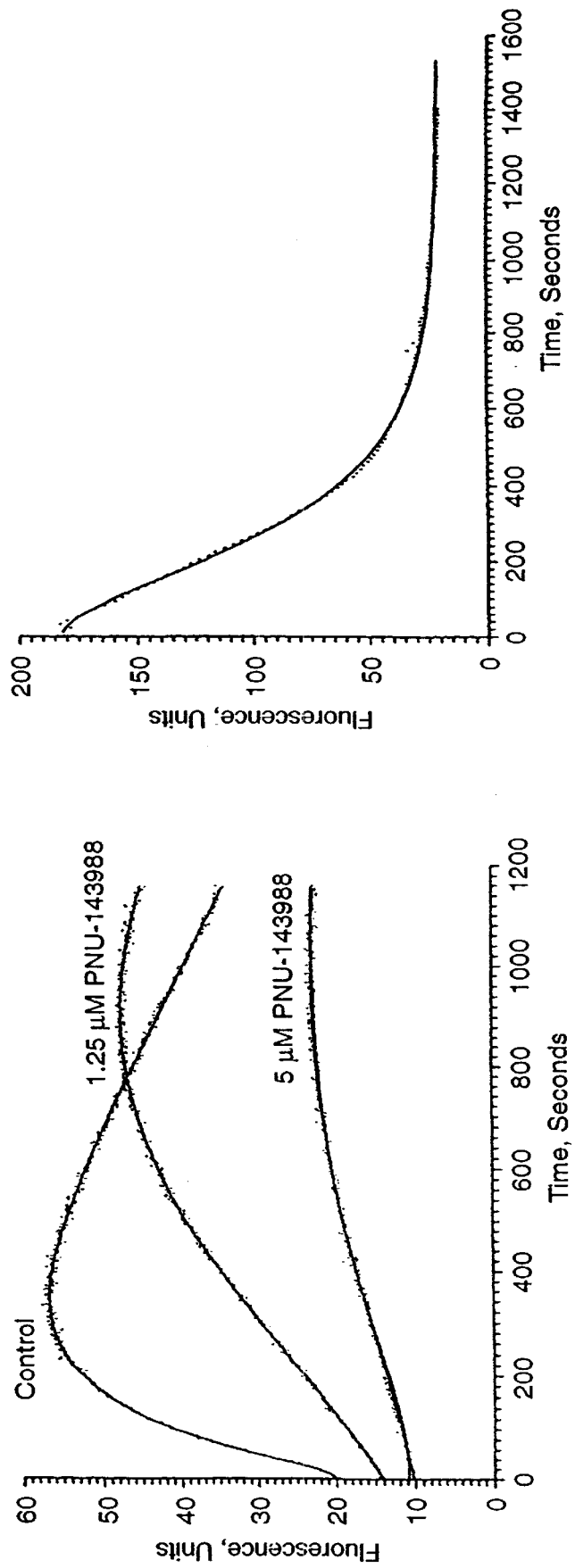

FIG. 10A. Time-Dependency of the isothermal denaturation of Stromelysin monitored by SYPRO Orange Fluorescence. The time-dependency of stromelysin isothermal denaturation at 75° C. with or without the addition of the competitive inhibitor PNU-143988 was followed by the increase in SYPRO Orange fluorescence as described in Examples. The data for the control reaction were analyzed using Equation 4, and those for the inhibited reactions with Equation 11. Representative data in the presence of 1.5 and 5 mM PNU-143988 are also shown. The solid lines represent the theoretical fits to the experimental data points.

FIG. 10B. Time-Dependency of the isothermal denaturation of Stromelysin monitored by Tryptophan Fluorescence. The time-dependency of the isothermal denaturation of stromelysin was monitored at T=75° C. with detection using the decrease in the intrinsic tryptophan fluorescence for detection. The data were analyzed using Equation 11. The solid lines represent the theoretical fits to the experimental data points.

Figure 11B:
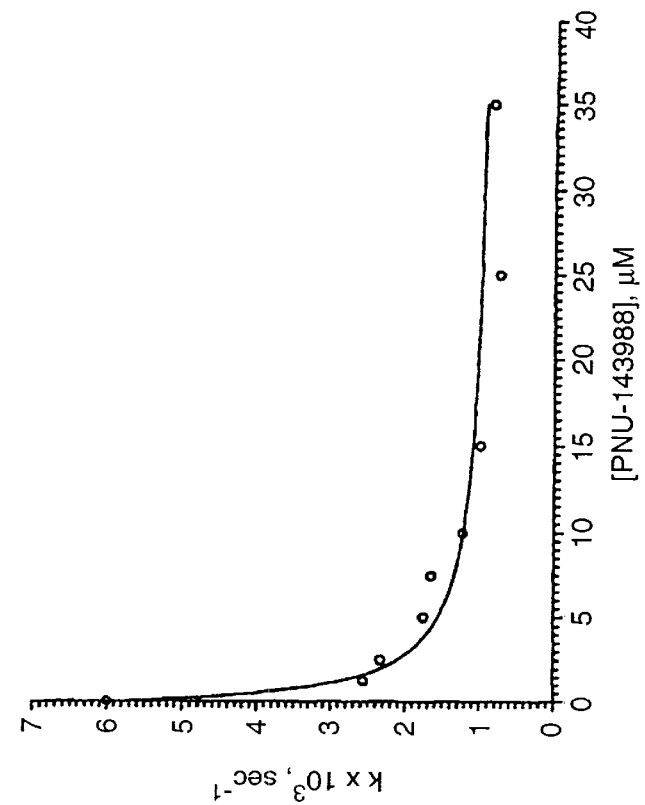
Figure 11A:
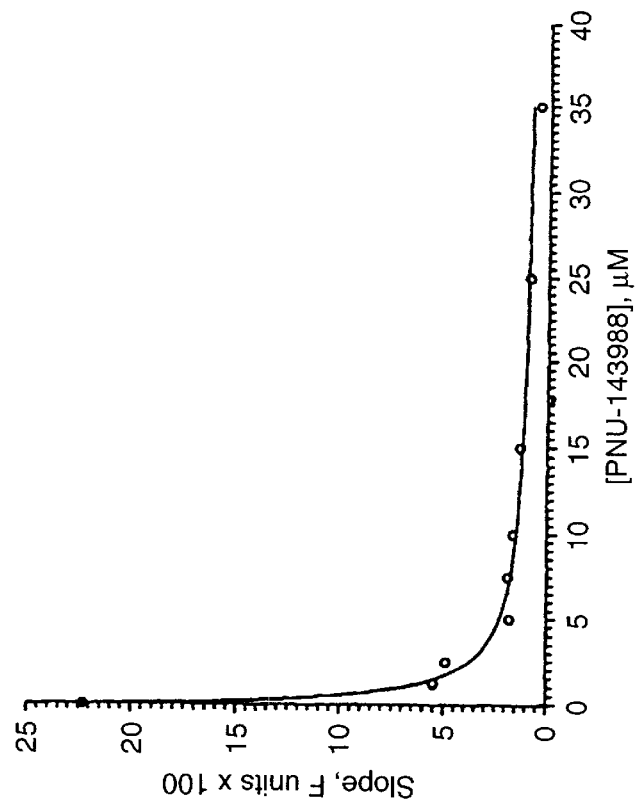

FIGS. 11A–11B. Effect of PNU-143988 on the Initial Rates and the Rate Constants of the Isothermal Denaturation of Stromelysin Monitored by SYPRO Orange. The time-dependency of stromelysin isothermal denaturation at 75° C. with or without the addition of the competitive inhibitor PNU-143988 was followed by the increase in SYPRO Orange fluorescence as described in the Methods. FIG. 11A= initial rates; FIG. 11B= rate constants.

DETAILED DESCRIPTION OF PREFERRED EMBODIMENTS

The present invention is directed to the use of isothermal denaturation. The methodology can be used to screen for ligands to a wide variety of molecules, particularly proteins, including those with unknown function. Significantly, the methods of the present invention eliminate the necessity of ramping temperatures up and down and should allow for much faster assay development and higher throughput in an HTS or UHTS automated environment. The technology should be easily expandable to looking for compounds that bind to RNA, DNA, α-acidic glycoprotein, and serum albumin, for example.

Isothermal denaturation offers an attractive alternative method for monitoring denaturation (e.g., unfolding of a target species) and for the identification of binding ligands. It is amenable to HTS and UHTS. Furthermore, the denaturation process is easily controllable, reproducible, and independent of the heating rate.

The choice of temperature used in isothermal denaturation can be determined by measuring the rate of denaturation of the target species at a series of temperatures (e.g., within a range of about 45° C. to about 75° C.). These measurements may be made, for example, using a fluorescent reporter molecule that binds to and reports conformational changes associated with the unfolding of the target molecule. Alternatively, denaturation signals can be monitored using UV absorbance, CD ellipticity, or by microcalorimetry studies with the target species, for example. Preferably, a preliminary DSC scan is run to determine $T_m$ (midpoint temperature) of the target species in appropriate buffers that enhance the stability of the target over a long period of time as would be known to one skilled in the art.

During the binding experiments, all components are maintained at one given temperature (preferably± about 0.2° C.) which is chosen to produce a slow, easily monitored denaturation of the target protein. If the temperature of isothermal denaturation is too low, the kinetics are too slow. Generally, it is desirable to have a detectable amount of denaturing (e.g., unfolding) occur within about 60 minutes or less. If the temperature is too high, the kinetics are so fast that the test compound would not be able to stabilize the denatured target species resulting, for example, in too great an extent of unfolding. Too much unfolding can cause aggregation that could result in precipitation of the target. Furthermore, at too high a temperature, the test compound may not bind at all. Preferably, the desired temperature for isothermal denaturing is equal to the $T_m$ value± about 10° C. of the target species as determined by DSC. More preferably, this temperature is equal to or up to about 10° C. less than the $T_m$ value of the target species.

The target species, preferably together with a suitable reporter molecule able to monitor its denaturation, is incubated in the presence and absence of the target species. In a preferred embodiment, the concentration of the compound and that of the reporter molecule are of comparable magnitude (preferably, no greater than about 1 $\mu$M), but may require the reporter molecule to be in excess relative to the target molecule, whereas the concentration of the test compound is in at least a 10-fold excess. The percent inhibition cutoff for a "hit" can be set prior to assay implementation, or determined statistically during or after all screening has been performed.

Fluorescence techniques are rapidly becoming the detection methods of choice for HTS and UHTS. Thus, in certain preferred embodiments of the present invention, fluorescence molecules are used as the markers of choice. Coupling fluorescence techniques with denaturation by isothermal methods is attractive because in isothermal denaturation the quantum yield of an extrinsically added reporter molecule is dependent only on changes in protein folding and not on temperature effects. Further, any change in the fluorescence quantum yield measures binding of the reporter molecule to different denatured forms of the target species. Thus, alteration of target stability by a bound ligand should be easily detectable.

The present invention demonstrates that isothermal denaturation can be used to determine if known competitive inhibitors/ligands could bind to target species. The results are comparable to those obtained by other methods. The agreement of the denaturation kinetics from three different detection methods confirms that the same unfolding processes are being measured using the methods of the present invention.

The fluorescence of the reporter molecule should preferably increase several-fold (preferably, at least about 2-fold) upon denaturation of the target. For proteins, this is typically accompanied by the exposure of the protein's hydrophobic regions. The reporter molecules should also preferably have low affinity for the native target; that is, the fluorescence of the native target/reporter molecule complex is linear over a wide concentration range or, preferably, does not bind to the native target at all so that it does not become a ligand itself. Finally, since compound libraries generally contain numerous compounds that absorb and/or fluoresce between about 300 nanometers (nm) and about 400 nm, the reporter molecule should preferably have excitation and emission in the visible region where few compounds interfere, e.g., excitation at about 488 nm and emission at about 515 nm.

Reporter molecules (e.g., fluorescent dyes) are commercially available from sources such as Molecular Probes (Eugene, Oreg.) and fluoresce brightly when bound to hydrophobic regions of the target molecule. These include SYPRO Orange, SYPRO Red, Nano Orange, Nile Red, 1-anilinonaphthalene-8-sulfonic acid (1,8-ANS), and dapoxylbutylsulfonamide (DBS) as well as other dapoxyl analogs. Nano Orange fluorescence provides an ultrasensitive dye for quantification of proteins in solution with a linear fluorescence range of about 10 nanograms/milliliter (ng/mL) to about 10 micrograms/milliliter ($\mu$g/mL) with a very low background fluorescence. SYPRO Orange and SYPRO Red are used for gel staining with sensitivity as good as silver staining. The basis for the increase in fluorescence of the dyes with protein denaturation is their binding to newly exposed hydrophobic sites. 1,8-ANS has been used extensively for many years to monitor the unfolding of proteins; however, its quantum yield when bound to the denatured protein is much lower than those of the dyes discussed above and, thus, would require the use of large quantities of protein and reporter molecule in the assays. DBS is a relatively new, solvatochromic dye whose fluorescence emission may shift as much as 100 nm upon changing the environment. Due to its lower excitation and emission wavelengths, however, it is less desirable than Nano Orange, SYPRO Orange, or SYPRO Red for HTS.

Any fluorescent reporter molecule whose emission intensity increases or decreases when bound to a desired target species can be used for isothermal denaturation. The affinity of a fluorescent reporter molecule toward a target species can be determined by measuring the fluorescence of a given concentration of the reporter molecule in the presence of increasing concentrations of the denatured target species and the native target species. Knowing the affinity then allows one to optimize the concentration of the fluorescent reporter molecule relative to the target species.

In addition to, or instead of, using noncovalent fluorescent reporter molecules that are added to a mixture of the test compound and target species, one may use target species labeled covalently with a pair of fluorophores, one of which quenches the fluorescence of the other. Because unfolding of the target species changes the intermolecular distances between the two fluorophores, the denaturation is accompanied by changes in fluorescence. By labeling the same target species at specific sites, the denaturation at different structural regions can be monitored.

Although fluorescence techniques, particularly dye binding resulting in fluorescence enhancement are the detection methods of choice, other techniques can be used in the methods of the present invention. This can include, for example, monitoring: 1) the change in UV absorbance, for example, at 280 nm resulting from exposure of aromatic amino acid(s) to solvent; 2) the change in molar ellipticity by circular dichroism (CD); 3) infra-red or NMR spectral shifts; 4) changes in mobility on a support material (e.g., solid support) such as size-exclusion chromatography, capillary electrophoresis, etc. None of these approaches necessarily requires the use of an extrinsic or intrinsic fluorescent reporter molecule.

For target species that have a relatively high denaturation temperature, the experiments can be performed in the presence of a chaotrope, such as urea, guanidine hydrochloride, organic solvents, or any other reagents that promote protein denaturation without unduly interfering with binding of the reporter molecule with the target species.

The exact experimental conditions for denaturation of each target molecule will vary. One skilled in the art can make appropriate decisions and/or experimentally determine appropriate buffer systems (pH, ionic strength, ionic co-factors, etc.). For example, the isolectric point (pI) of a protein molecule would help determine what pH would be useful in these studies.

In practice, the methods of the present invention can be carried out in a multi-reservoir sample holder, such as a microtiter plate. Typically, all components but the target species are added and the multi-reservoir sample holder is held at the appropriate temperature for a period of time. After thermal equilibrium is reached, the sample holder is preferably transferred to a station where the target species is added to all reservoirs, preferably simultaneously. The multi-reservoir sample holder is typically sealed prior to addition of any components. For example, a microtiter plate can include a covering that is made of a plastic sheeting which seals the plate but is scored in such a way that a microtiter tip easily penetrates it but that it re-closes after tip removal. After introduction of the target species, the sample holder is either transferred immediately to an appropriate detector for reading the denaturation signal or to an incubator for holding until detection is desired. All steps can be performed either manually or by robot as desired.

For high throughput screening, a commercially available Zymark/Zymate PCS system (Zymark Corp., Zymark Center, Hopkinton, Mass.) equipped with a Rapid Plate module, jacketed carousel, 10-plate incubator system interfaced with a fluorescent plate reader can be used. This system can process 96- and 384-well microtiter plates and can be adapted for use in the isothermal denaturation method of the present invention. For example, the 10-plate incubator can be modified with heating elements such as Watlow flexible flat mat heaters for sample incubation. The temperature of the incubator can be further controlled by the use of a circulating waterbath. The Zymark/Zymate system includes a jacketed carousel that can be modified to include a temperature controlled humidifier and fan internally, and heat lamps externally, to assist in temperature control and to reduce loss of sample volume in the microtiter plates. The Zymark/Zymate system also includes a pipetting station (Rapid Plate Module) that can be modified to include a heating block and heat lamps, for example. For fluorescence measurements, a BMG POLARstar microplate reader (BMG Labtechnologies, Inc., Durham, N.C.) can also be modified for control of temperature by a circulating waterbath (e.g., from about −20° C. to about 90° C.). This system is automated using robotics and computer software, which can be modified to allow for the samples to experience isothermal conditions.

Using the methods of the present invention, the kinetics of isothermal denaturation of thymidylate kinase (TK) and of stromelysin, with and without the presence of their specific ligands, were monitored by long-wavelength fluorescent dyes whose quantum yields increase when bound to exposed hydrophobic regions of unfolded proteins. The time dependencies were all consistent with a reaction scheme of two consecutive first-order reactions. That is, the kinetics of denaturation for both proteins were best described by a biphasic model. Thus, only two of the probably many steps are rate limiting. It is apparent that a significant amount of information of the kinetics of the unfolding processes are provided by the fluorescence measurements. The dependence of the rate constants on ligand concentration was analyzable in terms of a binding isotherm, reflecting the stabilizing effect of the protein/ligand complex. The method was validated by comparing its results with those obtained by steady-state fluorescence spectroscopy, circular dichroism, and UV spectrophotometry. The corresponding rate constants calculated from the results of the several analytical detection methods were comparable. The rate constants of both steps were dependent upon the binding of active-site ligands. The dissociation constants represent affinities of the ligands at the melting transition temperature. The affinity constants (i.e.,"dissociation constants") at physiological temperatures can be determined by extrapolation from measurements at two different temperatures. These results, coupled with those obtained in multi-well (e.g., 96-well) format, show that isothermal denaturation is a method of choice for HTS, including UHTS, for ligands with high specificity toward any given protein.

Having generally described the invention, the same will be more readily understood by reference to the following examples, which are provided by way of illustration and are not intended as limiting.

EXAMPLES

I. Materials and Methods

A. Reagents

SYPRO Orange, SYPRO Red, Nano Orange, 1-anilinonaphthalene-8-sulfonic acid (1,8-ANS), and dapoxylbutylsulfonamide (DBS) were purchased from Molecular Probes Inc., Eugene, Oreg. Thymidine monophosphate (TMP) and all other reagents were from Sigma-Aldrich Chemical Company. All commercial chemicals used were reagent grade or better. The compound referred to as PNU-143988 has the following structure:

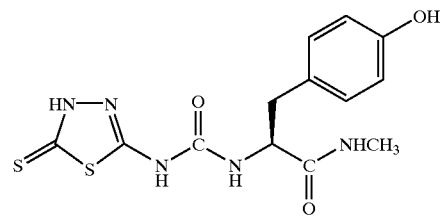

B. Proteins

S. aureus thymidylate kinase was cloned by Human Genome Sciences and purified by affinity chromatography using $Ni^{2+}$-NTA columns purchased from Qiagen (QIAGEN Inc., Valencia, Calif.). For TK the isothermal denaturation took place in a 5 millimolar (mM) Tris buffer, pH 7.80, containing 0.5 mM β-mercaptoethanol and was measured at a temperature of 53° C., with the exception of the validation experiments of the robotic assay which were carried out at 52° C. S. aureus uridylate kinase (UK) was cloned by Human Genome Sciences and purified by affinity chromatography using $Ni^{2+}$-NTA columns (QIAGEN Inc., Valencia, Calif.). UK has a transition midpoint, $T_m$, of 45.5° C. as determined by DSC using a buffer of 50 mM TRIS, 500 mM NaCl, 10% glycerol, and 5 mM β-mercaptoethanol, pH 7.8. Validation experiments for isothermal denaturation were performed at the $T_m$, 41° C., in pH 7.5 buffer composed of 50 mM Tris, 200 mM KCl, 10% glycerol, and 5 mM β-mercaptoethanol. Stromelysin was cloned and purified as described by Finzel et al., *Prot. Sci.,* 7; 2118–2126 (1998). It has a $T_m$ of 75° C. as determined by DSC. This temperature was chosen for the following isothermal denaturation experiments. The buffer system for stromelysin consisted of 10 mM imidazole, 2.5 mM $CaCl_2$, 5 micromolar (µM) $ZnCl_2$, pH 6.50.

C. Ligands

Stock solutions for all ligands were prepared in dimethylsulfoxide (DMSO) unless noted otherwise. Whenever the water solubility was high enough, secondary stock solutions were made in the buffer system for the particular protein; otherwise, diluted stocks were prepared in DMSO. A small aliquot of ligand solution, typically 10 µl or less, was added to buffer and equilibrated at the appropriate temperature in the cell before addition of the protein. Control experiments assessed the effect of added DMSO on protein denaturation. In some cases 0.1% CHAPS (weight/volume percent, (3-[(3-choloamidopropyl)-dimethylammonio]-1-propanesulfonate) was added to the reaction mixture to counteract the effects of DMSO. In order to validate the system, a subset of compounds which had been previously shown to be active in an activity assay for either thymidylate kinase or uridylate kinase was tested as a representative number of compounds having increased probability of being ligands for the protein targets.

D. Fluorescence Measurements

For fluorescence measurements, a photon counting ISS K2 spectrofluorometer in the ratio mode was used (ISS Inc., Urbana, Ill.). The temperature was maintained within 0.2° C. throughout the experiments by means of a Polysciences programmable temperature controller (Polysciences, Niles, Ill.). Emission was observed on the filter channel using the following emission filters: 530 nanometer (nm) bandpass filter for Nano Orange, 590 nm cut-off for SYPRO Orange, 630 nm cut-off for SYPRO Red and Nile Red, and 470 nm cut-off for 1,8-ANS and dapoxylbutyl-sulfonamide. Alternatively, fluorescence measurements were acquired by a BMG POLARstar microplate reader (BMG Labtechnologies, Inc., Durham, N.C.). Temperature was controlled with a circulating waterbath. This instrument best detected Nano Orange using a 485 nm center wavelength, 15 nm bandpass excitation filter and a 580 nm center wavelength, 12 nm bandpass emission filter.

The time-dependencies of the fluorescence of extrinsic dyes during isothermal denaturation were monitored as follows. The test dye was added to a stirred cuvette containing 2 milliliters (mL) of buffer that had been thermally preequilibrated at the desired temperature. A dye baseline was recorded for 45 seconds and the denaturation reaction initiated by the addition of a small aliquot of the protein stock solution. In this way, the protein reached the temperature of denaturation virtually instantaneously. In separate experiments, the protein was kept at the denaturation temperature in the absence of dye and the reporter molecule added at the end of the reaction. In the latter experiments, the fluorescence increase associated with the addition of dye was always instantaneous. In order to be certain that under the conditions of the experiment the dye itself would not complex a significant fraction of the native protein, a fixed amount of dye was titrated with increasing amounts of protein and showed that the fluorescence increase did not reach saturation.

The three tryptophan residues of stromelysin are buried in the active site region and as such are sensitive reporters of the unfolding of the protein. Thus, the isothermal denaturation of this protein was also measured by changes in the intrinsic tryptophan fluorescence. For these experiments, the protein was added to buffer equilibrated in a cuvette at the temperature of isothermal denaturation. The excitation wavelength was 293 nm and the emission was monitored using a 320±10 nm bandpass filter.

E. Calorimetric Measurements

DSC for stromelysin and TK was performed using an MC-2 differential scanning calorimeter from Microcal, Inc. (Northampton, Mass.). For stromelysin, the 1.2 mL sample cell of the calorimeter was filled with 150 µM enzyme in a pH 6.50 buffer containing 10 mM imidazole, 2.5 mM $CaCl_2$, and 5 mM $ZnCl_2$. For TK, the calorimeter cell was filled with 15 µM enzyme in a 50 mM Tris-HCl buffer, pH 7.70, containing 0.50 M NaCl, 10% glycerol, and 5 mM 2-mercaptoethanol. The reference cell was filled with the same buffer. The solutions were degassed for 5 minutes prior to scanning from 25° C. to 80° C. at a rate of 1° C./minute. Baseline scans, collected with dialysate buffer in the sample cell, were subtracted from the protein scans and the resulting data converted to unit protein concentration. The Y-axis of the instrument was calibrated using standard electrical heat pulses and the temperature scale was calibrated using n-octadecane and n-hexatriacontane which melt at 28.2° C. and 75.9° C., respectively.

F. Circular Dichroism

Circular Dichroism (CD) spectra were measured using a Jasco J-715 spectropolarimeter (Jasco Corp., Easton, Md.) and a cylindrical quartz cell with a pathlength of 0.1 centimeter (cm) thermostated to within 0.1 ° C. by a Haake D8 circulating water bath (Haake Gmbh, Karlsruhe, Germany). The concentration of the protein was chosen on the basis of its molar ellipticity and fell usually in the range of about 1 µM to about 20 µM. Solutions of protein or protein with 10- to 100-fold excess of ligand were prepared prior to injection into the cell. Each solution was first scanned at 22° C. from 178 nm to 260 nm with a response of 0.25 second, scan speed of 100 nm/minute, resolution and bandwidth of 1.0 nm and 5 accumulations. The cell was then rapidly heated to the temperature of isothermal denaturation and the time dependency of the ellipticity at 222 nm was monitored. Dichroism was sampled with a bandwidth of 1.0 nm at 0.5 millisecond (msec) intervals and accumulated for 16 seconds. Data were stored every one second as the running average of the 16 second bundles. After the time scan, a wavelength scan was performed at the same temperature. Cells and buffer solutions with and without ligand were routinely checked for absorbance and dichroism. Cells were thoroughly cleaned as described above and rinsed with distilled water and ethanol between experiments.

G. Absorbance Measurements

UV absorbance was measured using a Perkin-Elmer Lambda 40 UV-Vis dual-beam spectrophotometer (Perkin-Elmer Corp. Norwalk, Conn.). A capped 1.0 cm pathlength quartz cuvette filled with buffer was placed in the reference beam. In the sample beam, a capped 1.0 cm path length quartz cuvette containing 1.5 mL of degassed buffer or buffer plus ligand—less the volume of protein solution to be added—was placed in a thermostated cell holder and equilibrated at the temperature of isothermal denaturation. The temperature was maintained within 0.1° C. using a Neslab Exacal EX200 circulating water bath (Neslab Instruments, Inc. Portsmouth, N.H.). A 1–5 µL aliquot of the protein stock solution was added to the cuvette containing buffer or buffer plus ligand to yield a final volume of 1.5 mL and protein concentration near 0.5 µM. The cuvette was recapped and absorbance at 280 nm was measured every 1 second for up to 30 minutes with a bandwidth of 2 nm and response of 0.5 second. For each protein, the effects of several ligand concentrations were examined ranging from about 0.5 $\mu$M to about 400 $\mu$M. Cuvettes were thoroughly cleaned as described above with nitric acid and with 10% methanol and rinsed with distilled water and ethanol between experiments.

H. Data Analysis

Only in a few cases was the time dependency of protein denaturation an apparent first-order process. Those data were analyzed by a nonlinear least squares program using the equation:

$$Y=Y_o+\Delta Y\cdot(1-e^{-k_{exp}\cdot t}) \qquad \text{Equation 1}$$

where Y is the experimentally measured signal, $Y_o$ is the background signal, $\Delta Y$ is the total change in signal associated with the denaturation process, t is time and $k_{exp}$ is the experimentally measured apparent first-order rate constant. In general, the kinetics of denaturation displayed biphasic kinetics, often with a distinct induction period. Those time courses were analyzed according to the reaction scheme of two consecutive first-order reactions:

$$A \xrightarrow{k_1} B \xrightarrow{k_2} C \qquad \text{Equation 2}$$

where $k_1$, and $k_2$ are first-order rate constants and where, a priori, all three species contribute to the observed signal. The equation corresponding to the signal observed during these reactions is:

$$Y = Y_A \cdot e^{-k_1 t} + Y_B \cdot \frac{k_1}{k_2 - k_1}(e^{-k_1 t} - e^{-k_2 t}) + Y_C\left[1 + \frac{1}{k_1 - k_2}(k_2 e^{-k_1 t} - k_1 e^{-k_2 t})\right] \qquad \text{Equation 3}$$

where $Y_A$, $Y_B$, and $Y_C$ are the signals for the species A, B, and C, respectively. Often, it happened that within experimental error $Y_A=Y_B$, thereby simplifying the analysis since:

$$Y = Y_{A'} + (Y_C - Y_A)\left[1 + \frac{1}{k_1 - k_2}(k_2 e^{-k_1 t} - k_1 e^{-k_2 t})\right] \qquad \text{Equation 4}$$

When $Y_B=Y_C$, the experimental curve degenerates into a simple first-order rise or decay, depending on whether $Y_A>Y_B$ or $Y_B>Y_A$.

More often than expected, the preliminary analysis of the data by Equation 3 or Equation 4 indicated that $k_1$, and $k_2$ were very similar to each other. Since Equation 3 is not valid for the case where $k_1=k_2$, we integrated the system of rate equations:

$$\frac{dA}{dt} = -k \cdot A \qquad \text{Equation 5}$$

$$\frac{dB}{dt} = k \cdot A - k \cdot B \qquad \text{Equation 6}$$

$$\frac{dC}{dt} = k \cdot B \qquad \text{Equation 7}$$

to yield:

$$A=A_o\cdot e^{-k\cdot t} \qquad \text{Equation 8}$$

$$B=k\cdot A_o\cdot t\cdot e^{-k\cdot t} \qquad \text{Equation 9}$$

$$C=A_o\cdot[1-(k\cdot t+1)\cdot e^{-k\cdot t}] \qquad \text{Equation 10}$$

The time dependence of the signal is then given by:

$$Y=Y_a\cdot e^{-k\cdot t}+Y_B\cdot k\cdot t\cdot e^{-k\cdot t}+Y_C\cdot[1-(k\cdot t+1)e^{-k\cdot t}] \qquad \text{Equation 11}$$

This equation was used in conjunction with a nonlinear least squares to analyze the results of experiments with $k_1 \approx k_2$.

Robotic Assay

A library of compounds was tested in a high throughput screening mode in 96-well microtiter plate format with single compounds per well at the temperatures described above. The optimal dye and optimal ratio of dye to protein for TK and UK was assessed. Each microtiter plate contained 88 individual compounds and eight control wells that intially contained only buffer plus dye (no compound). These assay plates were manually sealed with a plastic 96-well microplate seal (Tomtec, Inc., Hamden, Conn.). These seals were scored for easy entrance of pipet tips, followed by reclosure after pipet tip exit. The remaining steps were carried out robotically as follows. Assay plates were deposited into the temperature/humidity-controlled incubator for an initial incubation period, typically 60–90 minutes, which equilibrated the assay plate to the desired assay temperature. A fluorescence measurement, $T_i$, was then taken by the BMG POLARstar to establish the lower bound of the assay. This fluorescent reading for those wells containing compounds plus buffer plus dye was used to ascertain the effect of the compounds themselves. Following an additional incubation period in a set of incubators which ensured that well contents were equilibrated to the assay temperature, assay plates were moved to the RapidPlate liquid dispensing unit. Protein was added from a plate reservoir to assay plates located on a modified heated plate position. For the final incubation, assay plates were transported back to the temperature/humidity-controlled incubator for a defined time at the assay temperature, typically 30 minutes. A second fluorescence measurement, $T_f$, was taken by the BMG POLARstar. The control wells (assay buffer plus dye plus protein) defined the upper bound of the assay. A comparison of the fluorescent measurement for the wells containing compound (plus assay buffer plus dye plus protein) compared to the control well reads at $T_i$ and $T_f$ defined which compounds bound to and stabilized the protein of interest.

II. Results

The temperature at which a given protein undergoes denaturation at an easily measurable rate was determined prior to the ligand binding studies. The rates were most appropriate for measuring methods at temperatures slightly below or at the thermal transition temperature ($T_m$) as measured by differential scanning calorimetry. To determine which fluorescent dye produces the largest signal for a given protein, a preliminary isothermal denaturation experiment at $T_m$ was performed with each dye at a concentration of 1 $\mu$M and the protein at 0.5 $\mu$M. The spectral properties of all dyes tested are given in Table 1. Due to their long excitation and emission wavelengths, Nano Orange, SYPRO Orange, and SYPRO Red are attractive for use in HTS format.

TABLE 1

Spectral Parameters Used in Measuring Isothermal Denaturation

| Dye | $\lambda_{exc}$, nm | $\lambda_{em}$, nm |
| --- | --- | --- |
| 1,8-ANS | 390 | 470 |
| Dapoxylbutylsulfonamide | 372 | 470 |
| Nile Red | 590 | 630 |
| Nano Orange | 490 | 525 |

TABLE 1-continued

Spectral Parameters Used in Measuring Isothermal Denaturation

| Dye | $\lambda_{exc}$, nm | $\lambda_{em}$, nm |
| --- | --- | --- |
| SYPRO Orange | 500 | 590 |
| SYPRO Red | 550 | 630 |

A. Thymidylate Kinase

The thermal scan for thymidylate kinase (TK), shown in FIG. 1, reveals a $T_m$ located at 53° C., the temperature which was then chosen for all subsequent isothermal experiments. Upon cooling and reheating of the protein, no observable peak was found (results not shown), which indicated that this protein had denatured irreversibly.

Fluorescence. FIG. 2 shows the results of preliminary experiments where the time-dependent fluorescence changes for each dye were measured in the presence of thymidylate kinase denaturing isothermally at 53° C. The fluorescence of all the dyes increased in a biphasic manner in the course of the denaturation, with DBS producing the largest net increase over background. The fluorescence of Nano Orange, SYPRO Orange, and SYPRO Red (used in general as protein quantitation and gel stain dyes) also increased significantly, while the fluorescence increase of 1,8-ANS, at a four-fold molar excess to protein, was relatively small. Finally, it was also ascertained that the increase in fluorescence of the amount of Nano Orange or SYPRO Orange used in the experiments upon addition of the native protein was linear over a wide range of protein concentrations (FIG. 3). These results demonstrate that the dyes do not saturate the protein under the conditions of the experiment. In other words, the dyes themselves do not compete with the ligands and they do not stabilize the protein to any measurable extent.

Because of its spectral properties (see Table 1), SYPRO Orange was chosen for use in further denaturation experiments. FIG. 4 shows representative time courses of SYPRO Orange fluorescence occurring during the isothermal denaturation of TK in the presence of increasing amounts of TMP, which is a specific ligand for the enzyme. When the protein was first denatured and the dye added at the end of the process, the fluorescence increase was instantaneous (data not shown). Thus, the time-dependency of the fluorescence changes represents protein unfolding and not a slow binding of the dye to the denatured protein. The time-dependencies were biphasic, indicating the presence of at least two rate-determining unfolding processes. The results were analyzed using a nonlinear least squares method with a variety of kinetic models. Of all the models tested, the model of two consecutive first-order reactions with identical rate constants, Equation 11, was the most consistent with the data. The agreement of the experimental points with the theoretical curves calculated with the best-fit parameters and Equation 11 is shown in FIG. 4.

The slope of the early, linear portion of the time course is also proportional to the first rate constant and, thus, either can be used to analyze the influence of TMP concentration on the denaturation rates. FIG. 5 shows the dependency of these two parameters on ligand concentration. The curves were analyzed using a nonlinear least squares method and equations corresponding to a variety of models relating denaturation rates to occupancy of the ligand binding site. The best consistency was found with the model where a fully cooperative binding of two TMP molecules per protein results in a six-fold stabilization of the enzyme (FIG. 5). This result is not fully surprising since thymidylate kinase is a dimeric protein as evidenced by size exclusion chromatography (E. coli protein is known to exist as a dimer in "Structure of thymidylate kinase reveals the cause behind the limiting step in AZT activation" by A. Lavie et. al. in Nature Structural Biology, 4,601–604 (1997)). From the slopes, $K_d$ was calculated to be 9.1±1.6 mM and from the rate constants $K_d$ was calculated to be 7.6±0.8 mM. These cooperative $K_d$ values, measured at 53° C., are not directly comparable to the noncooperative kinetic parameter $K_m$=27 μM determined at 25° C. by an activity assay using saturating ATP concentrations. It seems likely that the cooperativity arises from the fact that the kinetic mechanism of TK consists of an ordered addition, whereby TMP can only bind to the enzyme which has an occupied ATP site and that TMP can bind weakly to the ATP site.

Absorbance and Circular Dichroism. In order to ascertain that the fluorescence changes of the dyes actually are proportional to the two forms of denatured protein and do, in fact, measure the denaturation process, two other techniques, CD and UV absorbance, were employed to study the unfolding kinetics of the same protein.

Circular dichroism scans of the native protein and of its denatured form show that a significant change in the CD spectrum accompanies the unfolding (FIG. 6). For example, there was a 45% loss in intensity of the α-helical signal at 222 nm. Consequently, the time-dependency of the changes in molar ellipticity was monitored continuously at 222 nm. As illustrated in FIG. 7, the ellipticity at 222 nm increased rapidly and reached a maximum after about 10 minutes. Addition of 25 mM TMP, a natural ligand, greatly decreased both the rate and magnitude of the increase in ellipticity. The data were fully consistent with a simple first-order reaction, thereby indicating that the major changes in ellipticity are produced by the first of the two consecutive unfolding steps.

Finally, the time-dependent changes in hyperchromicity at 280 nm which result from the increase in solvent exposure of aromatic amino acids were measured. The data in FIG. 8 show that the hyperchromic changes associated with the unfolding of TK were rapid and biphasic. The absorbance data were best fit by a model of two consecutive first-order reactions. The results were most consistent with a model of two consecutive first-order reactions, but with unequal rate constants, as described by Equation 3.

The rate constants obtained by the three techniques are compared in Table 2. Due to spectral interference, the effects of the presence of TMP on the changes in hyperchromicity were not tested. It appears that the physical properties measured by all these methods do undergo a significant change during the first rate-limiting step. There was good agreement between the rate constants of the first step, $k_1$, indicating that all three methods are measuring the same process. On the other hand, the second step observed by SYPRO Orange does not produce any changes in hyperchromicity and the second, very slow step observed by hyperchromicity does not have any changes in SYPRO Orange fluorescence associated with it.

TABLE 2

Rate Constants for Thymidylate Kinase Denaturation at 53° C.
Measured by Various Methods

| Method | $k_1 \times 10^3$, sec$^{-1}$ | $k_2 \times 10^3$, sec$^{-1}$ |
| --- | --- | --- |
| Circular dichroism[@] | 12.0 ± 0.04 | NA |
| Absorbance at 280 nm[*] | 17.0 ± 0.20 | 2.90 ± 0.09 |
| SYPRO Orange fluorescence[#] | 17.0 ± 0.09 | 17.0 ± 0.09 |

[@]First-order reaction;
[*]Calculated using Equation 4;
[#]Calculated using Equation 11.

B. Stromelysin

Both the CD spectrum (Sarver et. al., *BBA*, 1434, 304–316 (1999)) and the tryptophan fluorescence (Epps et al., *J. Prot. Chem.*, 17, 699–712 (1998)) of stromelysin are affected by the binding of ligands to the active site. DSC revealed that this protein has an extremely high $T_m$ at 75° C. as shown in FIG. 9. Also, DSC experiments showed an increase of as much as 15° C. in the $T_m$ for ligand-bound (Sarver et. al., *BBA*, 1434, 304–316 (1999)). Thus, the structure of stromelysin appears to lend itself to isothermal denaturation studies in that ligand binding dramatically affects the unfolding process. Even the tryptophan fluorescence should be a useful tool for monitoring the denaturation processes.

Fluorescence. The time-dependency of the denaturation of stromelysin was biphasic at 75° C. as monitored using SYPRO Orange and (shown in FIG. 10A). The denaturation was rapid and was inhibited in a dose-dependent manner by PNU-143988, a known thiadiazole-type competitive inhibitor.

The denaturation reaction in the absence of ligands was most consistent with a model of two consecutive first-order reactions with two unequal rate constants (Equation 3) followed by a linear downward drift. The linear drift most likely derives from aggregation and/or precipitation of the denatured protein. It was absent in the denaturation which occurred in the presence of inhibitors. Analysis of the data showed that the best kinetic model is the one with two consecutive first-order rate model with identical rate constants (Equation 11). The rate constants calculated from these analyses are given in Table 3.

TABLE 3

Rate Constants for Stromelysin Denaturation at 75° C.
Measured by Various Methods.

| Method | $k_1 \times 10^3$, sec$^{-1}$ | $k_2 \times 10^3$, sec$^{-1}$ |
| --- | --- | --- |
| SYPRO Orange Fluorescence | 60.2 ± 1.8 | 7.49 ± 0.04 |
| Tryptophan Fluorescence | 67.7 ± 1.2 | 6.77 ± 0.12 |
| Absorbance | 50.2 ± 1.8 | NA |

The intrinsic tryptophan fluorescence of stromelysin is particularly sensitive to ligand-induced conformational changes, and, presumably, to denaturation of the active-site region. As shown in FIG. 10B, there was a rapid, biphasic loss of the tryptophan fluorescence intensity over the time course of the isothermal denaturation at 75° C. The time-dependency of the decay of the tryptophan fluorescence was most consistent with a model of two consecutive first-order reactions with identical rate constants (Equation 11). This model yielded rate constants that were in excellent agreement with those measured by the fluorescence increase of SYPRO Orange under the same conditions (Table 3).

Two parameters derived from the fluorescence kinetic curves measure the rate of denaturation, namely, the slope at the inflection point, and the first-order rate constant. The values of both parameters decreased in the presence of inhibitors in a saturable, dose-dependent manner, as shown in FIG. 11 for the case of fluorescence measurements. The concentration dependencies were consistent with a model where binding of the inhibitor results in a drastic decrease in the rate of denaturation. The data were analyzed in terms of a simple Langmuir binding isotherm model, yielding $K_d = 0.28 \pm 0.02$ μM from the initial rates and $K_d = 0.35 \pm 0.13$ μM from the rate constants. These values, measured at 75° C., are quite comparable to the value of $K_d = 0.40$ μM measured by a rate assay at 25° C.

Absorbance. Isothermal denaturation of stromelysin in the presence and absence of PNU-143988 revealed a dose-dependent inhibition of both the rate and magnitude of the hyperchromicity changes (data not shown). The hyperchromicity reached a maximum in three minutes and declined slightly at longer periods of treatment while PNU-143988 extended in a dose-dependent manner the time needed for full reaction. The simplest model consistent with the experimental data of the uninhibited reaction was a simple first-order reaction and the best-fit rate constant was comparable to that of the first step of the two-step denaturation process measured by the other techniques (Table 3).

Validation of Robotic HTS Assay. Prior to validation experiments, the optimal dye and optimal ratio of dye to protein was determined in 96-well microtiter plate format for both TK and UK isothermal denaturation under the assay conditions described above. Isothermal denaturation of TK was best detected with Nano Orange at final assay concentrations of 0.4 μM protein and 1.1 μM dye. In the same manner, Nano Orange was utilized to obtain a sufficient window to allow detection of the isothermal denaturation of UK with final assay concentrations of 0.4 μM protein and 0.8 μM dye.

In order to demonstrate the validity of isothermal denaturation as a HTS robotic assay, denaturation of TK and UK was performed in the presence of a known ligand in microplate format with the assay operating robotically as described. The ligands used were TMP, in the case of TK, and uridine monophosphate (UMP), in the case of UK. The proteins were subjected to the assay's denaturing conditions either in the absence of (control) or presence of increasing ligand concentration. Using $T_i$ and $T_f$ fluorescence measurements, percent inhibition was calculated, as one skilled in the art would do. For thymidylate kinase, increasing concentrations of TMP decreased the denaturation of the protein, as expected based on results seen in cuvette experiments. A curve of TMP concentration versus calculated percent inhibition of control was fit with a Langmuir binding isotherm model, yielding an apparent $K_d$ value similar to what has been seen previously when taking error into account. Similarly for uridylate kinase, the effect of UMP on the denaturation was concentration-dependent, as concentration of UMP increased, denaturation decreased. Data was analyzed in terms of a Langmuir model. Resulting calculations gave an apparent $K_d$ value of 5.76±0.95 mM which was comparable to the apparent $K_d$ value of 1 mM obtained from an activity assay carried out at 25° C.

Validation of the HTS system was furthered by the isothermal denaturation of TK and UK in the presence of a subset of compounds with an increased potential of containing protein ligands since these compounds had inhibitory activity in activity assays. This validation test was performed as described with 10 μM final compound concentration. Using the $T_i$ and $T_f$ measurements, percent inhibition was calculated. True actives were determined by using three standard deviations from the mean of the assay plate controls as the active cutoff value. Results are shown in Table 4. Control experiments were also conducted. Compounds with intrinsic spectral properties including fluorescence and quench were observed in these experiments.

TABLE 4

Results of the HTS Validation Test.

| Protein Target | Number of Compounds Tested | Number of Actives |
|---|---|---|
| TK | 703 | 83 |
| UK | 703 | 97 |

C. *Staplhylococcus aureus* FemA

*S. aureus* FemA (Ehlert et al., *J. Bacteriol.*, 179, 7573–7576 (1997) and Tschierske et al., *FEMS Microbiol. Lett.*, 153, 261–264 (1997)) is a protein presumably involved in cell wall biosynthesis and thus provides an attractive target as a potential antibacterial. The protein is expressed with a 6-his tag so that it can be purified with Qiagen $Ni^{2+}$-NTA columns as for thymidylate kinase described above. A pH sufficiently removed from the isoelectric point (pI value) is chosen for the buffer in which the protein is solubilized; in addition appropriate ionic strength and cations are used so that maximal structure can be obtained as monitored, e.g., in CD ellipticity studies.

Since this protein has no known biochemical function, isothermal denaturation provides an ideal way to discover compounds that bind to this protein. It is believed that this protein exhibits multi-phasic kinetics similar to those observed with thymidylate kinase and stromelysin. The $T_m$ value is determined by differential scanning calorimetry studies. The detailed kinetic pathway of denaturation must first be determined by fluorescence, absorbance, and/or another physical method as described above. The optimal dye and optimal ratio of dye to protein is rapidly assessed in a 96-well microtiter plate format. The fluorophore used is SYPRO Red.

A library of compounds (>100,000) are tested in a high throughput screening mode in 96-well microtiter plate format with single compounds per well at or, at most, 5° C. below the $T_m$ value. Each microtiter plate contains 88 individual compounds. Furthermore, eight control wells exist in the plate that intially contain only buffer plus dye (no compound). Prior to addition of protein, the microtiter plate containing compounds plus control wells are read ($T_i$ read) which establishes the lower bound of the assay. This fluorescent reading for those wells containing compounds plus buffer plus dye is used to ascertain the effect of compounds themselves.

After a time at the assay temperature, e.g., 30 or 60 minutes, another fluorescent measurement is performed ($T_f$ read). The control wells (assay buffer plus dye plus protein) define the upper bound of the assay. A comparison of the fluorescent values for those wells with compound (plus assay buffer plus dye plus protein) compared to the fluorescent values of the control wells at $T_i$ and $T_f$ defines which compounds bind to and stabilize the protein of interest, which in this example is *S. aureus* FemA. Only those compounds that demonstrate stabilization in a subsequent repeat experiment are pursued as potential ligand binders.

In addition to compounds that truly bind to femA, a compound could give enhanced fluorescence because it: 1) is a hydrophobic compound that could bind dye; 2) may have intrinsic fluorescence at the wavelengths used; 3) could form micelles; or 4) could be a denaturant, destabilizer, etc. Similarly, a compound could have binding activity but exhibit lower than expected results because the compound adsorbs light (quenches) at the wavelengths tested.

To eliminate compounds that affect dye directly, compound plus dye plus buffer at the assay temperature are read before the addition of protein. Any compounds that have intrinsic fluorescence, quench, fluorescence enhancement or fluorophore sequestration can thus be identified. To assess those compounds which enhance protein denaturation, an additional study is performed after the screen has been performed. The effect of compound on dye binding to the target molecule is performed at ambient temperature. Any compound which is a denaturant demonstrates enhanced binding of the fluorescent dye to the protein even when no thermal denaturation of the protein occurs. Compounds of this type would only be of interest if they exhibited this property for a specific protein (target) and did not affect two or more proteins (targets) in this manner.

After all these criteria are met, those compounds that are putatively true binders can then be further characterized. The first study would be to ascertain whether the compounds exhibit a reasonable dose-response. Additionally the effect of these compounds on the kinetics of protein denaturation can be studied and consequently $K_d$ values can be determined. To determine $K_d$ values at a given temperature, ligand dose-response curves for the full time-course kinetics are run. This process must be performed at three or more temperatures. Then, assuming Arrhenius behavior, the $K_d$ of the compound can be obtained for any temperature.

In addition to screening of an entire library of individual compounds, compound mixtures can be tested. A subset of the entire library that contains mixtures of eight compounds per microtiter plate well are used. The assay is carried out as described above. The compounds for those mixtures that demonstrate the appropriate results are then identified and tested individually. In this case positive results could occur in mixtures but not for individual compounds because the results could be additive, or more likely, synergistic. Consequently, if assays with individual compounds are not active, permutations of mixtures can be tested to determine which combination gives the original screening result.

D. *S. aureus* Unknown Gene Product

In addition to screening an entire compound collection, subsets of a library or "sublibraries," based upon rationale criteria can be tested. The advantage of using a sublibrary (ies) is to accelerate the discovery of a useful compound from high throughput screening. In this example another protein target is utilized, *S. aureus* Unknown Gene Product. This protein is an essential gene product for this organism. A genetically engineered strain of *S. aureus* that has this function eliminated prevents bacerial growth. However, its biological/biochemical function is unkown; and although searching of genomic database identifies similar genes in other micro-organisms, they also have no known biological or biochemical function. Because the DNA sequence for this gene is known, constructs can be engineered placing a 6-his tag at either the amino- or caboxyl-terminal end of the protein and purified as described for the other 6-his tagged proteins described. Maximal structure under given experimental conditions as monitored, for example, by CD can be obtained, similar to the femA protein described above.

One specific sublibrary tested, the dissimilarity sublibrary, is generated by a dissimilarity search in which compounds are sorted on their structural/chemical properties. The most dissimilar compounds are selected but, similutaneously, they represent the diversity of the entire library. Compounds identified that stabilize this protein target in isothermal denaturation studies are tested further in their own right. In addition, compounds in the library with similarity to these ligand-binders can be selected from the entire library by using computer search programs. These are also tested. In this way the active compounds could potentially be identified by screening only a limited subset of the entire compound collection.

E. Nucleic Acid Isothermal Denaturation

Oligodeoxyribonucleotides that contain the sequence of interest can be synthesized or purchased commercially and assembled into duplex DNA in the proper order. The assembled DNA can then be inserted into an expression system (e.g. MEGAScript from Ambion) to generate an RNA of interest. Alternatively, if the RNA of interest is sufficiently small, the oligos can be constructed to contain an appropriate promoter such that in vitro transcription can be done without any cloning and expression steps. Isolation of RNA can be obtained by protocols known to anyone skilled in molecular biologic arts.

As for proteinaceous targets, a $T_m$ can be determined experimentally with DSC. Examples of extrinsic fluorescent dyes that can be used to monitor the transition from an ordered to a disordered RNA structure include SYBR Green, SYBR GreenII, Pico-Green, and TOPRO, YOYO, etc. Examples of RNA molecules that can be used to demonstrate this approach include: 1) HIV-1 tar 47–86 (Mei et al., *Biochemistry*, 37,14204–14212 (1998)); 2) RNA aptamer J6fl (Cho et al., *Biochemistry* 37, 4985–4992 (1998)); and 3) A-site of 16s rRNA (Wong et al., *Chemistry and Biology*, 5, 397–406 (1998)). Ligands known to bind to these respective RNA molecules are: 1) Neomycin, other aminoglycoside antibiotics, and other compounds (Mei et al., *Biochemistry*, 37, 14204–14212 (1998)); 2) tobramycin ((Cho et al., *Biochemistry*, 37, 4985–4992 (1998)); and 3) Kanamycin and other aminoglycides (Wong et al., *Chemistry and Biology*, 5, 397–406 (1998)).

Just as known ligands for proteinaceous targets stabilize their structures under isothermal conditions, these known ligands stabilize their cognate RNA molecules under similar conditions. Similarly, as for protein targets, a large collection of compounds can be tested in high throughput screening to determine whether any might bind to, and stabilize, these nucleic acid structures under isothermal denaturation conditions. These compounds can be tested singly or as combinations of several compounds. In addition to monitoring isothermal denaturation with these fluorescent dyes, one skilled in the art could also monitor these changes using UV hyperchromicity or capillary electrophoresis.

It will be clear that the invention may be practiced otherwise than as particularly described in the foregoing description and examples. Numerous modifications and variations of the present invention are possible in light of the above teachings and, therefore, are within the scope of the invention. The entire disclosure of all publications, patents, and patent applications cited herein are hereby incorporated by reference.

What is claimed is:

1. A system for determining whether a test compound is capable of binding a target species under isothermal denaturing conditions, comprising:

(a) a compartment comprising a mixture comprising;
  (i) at least one test compound; and
  (ii) a least one target species, wherein the isothermal denaturing conditions are effective to cause at least a portion of the target species to denature to a measurable extent;
(b) means for providing isothermal denaturing conditions; and
(c) means for detecting a denaturation signal of each target species in the presence of at least one test compound, whereby a decrease in the denaturation signal of the target species in the presence of the at least one test compound as compared to a denaturation signal of the species in the absence of the at least one test compound is an indication of binding between the target species and the at least one test compound.

2. The system of claim 1 wherein the target species is a polypeptide or polynucleotide.

3. The system of claim 2 wherein the target species is a protein.

4. The system of claim 1 wherein the compound binds specifically to the target species.

5. The system of claim 1 wherein the compound binds to the target species through covalent, hydrophobic, ionic, or hydrogen bonding interactions.

6. The system of claim 1 wherein detecting the denaturation signal comprises detecting a fluorescence signal, a change in UV absorbance, a change in molar ellipticity, a spectral shift in an infra-red spectrum, a spectral shift in an NMR spectrum, or a change in mobility on a support material.

7. The system of claim 6 wherein detecting the denaturation signal comprises detecting a fluorescence signal.

8. The system of claim 1 wherein the isothermal denaturation conditions comprise a temperature equal to or about 10° C. more or less than the $T_m$ value of the target species as determined by differential scanning calorimetry.

9. The system of claim 8 wherein the isothermal denaturation conditions comprise a temperature equal to or up to about 10° C. less than the $T_m$ value of the target species as determined by differential scanning calorimetry.

10. The system of claim 1 further comprising incubating at least one test compound, at least one target species, and at least one reporter molecule under isothermal denaturing conditions.

11. The system of claim 1 wherein the concentrations of the test compound and the reporter molecule are of comparable magnitude.

12. The system of claim 11 wherein the concentration of the test compound is in at least a 10-fold excess relative to the concentration of the target species.

13. The system of claim 10 wherein the reporter molecule is a fluorescent reporter molecule.

14. The system of claim 1 wherein each test mixture includes one target species.

15. The system of claim 1 wherein each test mixture includes at least two test compounds.

16. The system of claim 15 wherein each test mixture includes two to ten test compounds.

* * * * *

UNITED STATES PATENT AND TRADEMARK OFFICE
CERTIFICATE OF CORRECTION

PATENT NO. : 6,713,260 B2
DATED : March 30, 2004
INVENTOR(S) : Tomich et al.

It is certified that error appears in the above-identified patent and that said Letters Patent is hereby corrected as shown below:

<u>Title page,</u>
Item [57], ABSTRACT, please delete entire abstract and insert the following new abstract:
-- A high throughout screening method for identifying a compound that binds to a target species. The method includes: incubating a plurality of test mixtures under isothermal denaturing conditions, each test mixture including at least one test compound and at least one target species, wherein the isothermal denaturing conditions are effective to cause at least a portion of the target species to denature to a measurable extent. The method further involves detecting a denaturation signal of each target species in the presence of the at least one test compound; and comparing the denaturation signal of each target species in the presence of the at least one test compound with a denaturation signal of the same target species in the absence of the at least one test compound under the same isothermal denaturing conditions. --

<u>Column 3,</u>
Line 47, delete "mM" and insert -- $\mu M$ --
Line 49, after "protein." insert -- The data were analyzed using Equation 11 and the solid lines represent the theoretical fits to the experimental data. --

<u>Column 4,</u>
Line 15, delete "Methods." and insert -- Examples. --
Line 25, delete "mM" and insert -- $\mu M$ --
Line 41, delete "Methods" and insert -- Examples --

<u>Column 10,</u>
Line 24, delete "n-octadecane and n-hexatriacontane" and insert -- *n*-octadecane and *n*-hexatriacontane --

<u>Column 11,</u>
Lines 27-28, delete "a priori" and insert -- *a priori* --
Equation 4, delete "Y=$Y_A$" and insert -- Y=$Y_A$ --

<u>Column 12,</u>
Equation 11, delete "Y-$Y_\alpha$.e" and insert -- Y=$Y_A$.e --

<u>Column 17,</u>
Line 43, delete "$T_m$." and insert therefor -- $T_m$ --

UNITED STATES PATENT AND TRADEMARK OFFICE
CERTIFICATE OF CORRECTION

PATENT NO.     : 6,713,260 B2
DATED          : March 30, 2004
INVENTOR(S)    : Tomich et al.

It is certified that error appears in the above-identified patent and that said Letters Patent is hereby corrected as shown below:

Column 18,
Line 52, delete "bacerial" and insert -- bacterial --
Line 53, delete "unkown;" and insert -- unknown --
Line 58, delete "caboxyl" and insert -- carboxyl --
Line 67, delete "similutaneously" and insert -- simultaneously --

Column 19,
Line 17, delete "in vitro" and insert -- *in vitro* --

Signed and Sealed this

Tenth Day of August, 2004

JON W. DUDAS
*Acting Director of the United States Patent and Trademark Office*